(12) United States Patent
Mathuis et al.

(10) Patent No.: US 11,067,379 B2
(45) Date of Patent: Jul. 20, 2021

(54) DIGITAL HOLOGRAPHIC MICROSCOPE WITH ELECTRO FLUIDIC SYSTEM, SAID ELECTRO-FLUIDIC SYSTEM AND METHODS OF USE

(71) Applicant: Ovizio Imaging Systems NV/SA, Brussels (BE)

(72) Inventors: Philip Mathuis, Asse (BE); Serge Jooris, Gistoux (BE)

(73) Assignee: Ovizio Imaging Systems NV/SA, Brussels (BE)

( * ) Notice: Subject to any disclaimer, the term of this patent is extended or adjusted under 35 U.S.C. 154(b) by 924 days.

(21) Appl. No.: 15/408,858

(22) Filed: Jan. 18, 2017

(65) Prior Publication Data
US 2017/0205222 A1 Jul. 20, 2017

(30) Foreign Application Priority Data
Jan. 19, 2016 (EP) .................................... 16151897

(51) Int. Cl.
*G01N 1/00* (2006.01)
*G01B 9/02* (2006.01)
(Continued)

(52) U.S. Cl.
CPC ........... *G01B 9/02047* (2013.01); *G01N 1/14* (2013.01); *G01N 15/14* (2013.01); *G01N 15/147* (2013.01);
(Continued)

(58) Field of Classification Search
CPC ........................................................ G01N 1/00
See application file for complete search history.

(56) References Cited

U.S. PATENT DOCUMENTS 4,786,594 A 11/1988 Khanna et al.
5,089,416 A 2/1992 Schwartz
(Continued)

FOREIGN PATENT DOCUMENTS

CN 202 808 799 3/2013
EP 0479231 A1 4/1992
(Continued)

OTHER PUBLICATIONS

Extended European Search Report for European Patent Application No. 16151897.2, dated Jul. 21, 2016.
(Continued)

*Primary Examiner* — Jyoti Nagpaul
(74) *Attorney, Agent, or Firm* — Knobbe, Martens, Olson & Bear, LLP

(57) ABSTRACT

The current invention concerns a fluid microscope system for analyzing and/or monitoring the contents of one or more fluid-based reactors or canalizations such as bio-reactors, micro-reactors, brewing reactors, water supply systems or sewer systems. The fluid microscope system includes a digital holographic microscope (DHM) with one or more electro-fluidic systems, capable of guiding fluid from the reactors to the DHM. The current invention also concerns an electro-fluidic system for such a fluid microscope system having any or all of the elements mentioned above. Furthermore, the current invention encompasses a method for installing, replacing and removing such an electro-fluidic system in and from a fluid microscope system, and lastly, a method for monitoring and/or observing suspended objects in a fluid in a fluid-based reactor or canalization.

11 Claims, 4 Drawing Sheets

(51) Int. Cl.
  *G01N 15/14* (2006.01)
  *G03H 1/04* (2006.01)
  *G01N 1/14* (2006.01)
  *G01N 21/27* (2006.01)

(52) U.S. Cl.
  CPC ........ *G01N 15/1484* (2013.01); *G01N 21/272* (2013.01); *G03H 1/0443* (2013.01)

(56) References Cited

U.S. PATENT DOCUMENTS

| | | |
|---|---|---|
| 5,243,409 A | 9/1993 | Sagner |
| 5,256,571 A | 10/1993 | Hurley et al. |
| 5,495,333 A | 2/1996 | Konda |
| 6,249,345 B1 | 6/2001 | Kraack |
| 6,327,377 B1 | 12/2001 | Rutenberg |
| 6,361,934 B1 | 3/2002 | Acton |
| 6,394,966 B1 | 5/2002 | Gill |
| 6,651,008 B1 | 11/2003 | Vaisberg et al. |
| 6,809,862 B2 | 10/2004 | Behnsen et al. |
| 6,924,094 B1 | 8/2005 | Gingeras et al. |
| 6,954,667 B2 | 10/2005 | Treado |
| 7,009,700 B2 | 3/2006 | Dubois et al. |
| 7,286,222 B2 | 10/2007 | Gardner |
| 7,616,320 B2 | 11/2009 | Javidi et al. |
| 8,599,383 B2 | 12/2013 | Teitell |
| 9,569,664 B2 | 2/2017 | Judkewitz |
| 9,675,974 B2 | 6/2017 | Jooris et al. |
| 9,684,281 B2 | 6/2017 | Mathuis et al. |
| 9,846,151 B2 | 12/2017 | Magniette |
| 9,904,248 B2 | 2/2018 | Mathuis et al. |
| 2002/0064328 A1 | 5/2002 | Neuberger |
| 2002/0106119 A1 | 8/2002 | Foran |
| 2002/0164063 A1 | 11/2002 | Heckman |
| 2003/0113832 A1 | 6/2003 | Lauf |
| 2003/0199649 A1 | 10/2003 | Orbison et al. |
| 2005/0036181 A1 | 2/2005 | Marquet et al. |
| 2005/0272103 A1 | 12/2005 | Chen |
| 2006/0014239 A1 | 1/2006 | Luttmann et al. |
| 2006/0088814 A1 | 4/2006 | Hecht et al. |
| 2006/0132799 A1 | 6/2006 | Franck et al. |
| 2006/0283945 A1 | 12/2006 | Excoffier |
| 2007/0216906 A1 | 9/2007 | Javidi et al. |
| 2008/0018966 A1 | 1/2008 | Dubois et al. |
| 2008/0032325 A1 | 2/2008 | DiMarzio |
| 2008/0113340 A1 | 5/2008 | Schlegel |
| 2008/0137933 A1 | 6/2008 | Kim |
| 2008/0242556 A1 | 10/2008 | Cao et al. |
| 2009/0082637 A1 | 3/2009 | Galperin |
| 2009/0092227 A1 | 4/2009 | David |
| 2009/0244667 A1 | 10/2009 | Frentz |
| 2009/0296083 A1 | 12/2009 | Saski et al. |
| 2009/0305393 A1 | 12/2009 | Joeris |
| 2010/0034442 A1 | 2/2010 | Minakuchi |
| 2010/0196871 A1 | 8/2010 | Dodgson |
| 2010/0315501 A1 | 12/2010 | Ludwig |
| 2011/0134426 A1 | 6/2011 | Kaduchak |
| 2011/0204256 A1 | 8/2011 | Patt |
| 2011/0212440 A1* | 9/2011 | Viovy ............... B01L 3/502761 435/6.1 |
| 2012/0015391 A1 | 1/2012 | Zhang et al. |
| 2012/0200901 A1 | 8/2012 | Dubois |
| 2012/0218379 A1 | 8/2012 | Ozcan |
| 2014/0038171 A1 | 2/2014 | Metzger et al. |
| 2014/0049634 A1 | 2/2014 | Tafas |
| 2014/0193850 A1 | 7/2014 | Jooris et al. |
| 2014/0195568 A1 | 7/2014 | Mathuis et al. |
| 2014/0329231 A1 | 11/2014 | Magniette |
| 2014/0349336 A1 | 11/2014 | Magniette |
| 2014/0376816 A1 | 12/2014 | Lagae et al. |
| 2015/0056607 A1 | 2/2015 | Jooris et al. |
| 2015/0248109 A1 | 9/2015 | Mathuis et al. |
| 2017/0023472 A1 | 1/2017 | Pavillion et al. |
| 2017/0261930 A1 | 9/2017 | Mathuis et al. |

FOREIGN PATENT DOCUMENTS

| | | |
|---|---|---|
| EP | 1524491 A1 | 4/2005 |
| EP | 2008715 A1 | 12/2008 |
| EP | 2602608 | 6/2013 |
| EP | 2602608 * | 12/2013 |
| WO | WO 98/57152 | 12/1998 |
| WO | WO 99/44593 A1 | 9/1999 |
| WO | WO 2004/057464 A2 | 7/2004 |
| WO | WO 2004/102111 A1 | 11/2004 |
| WO | WO 2006/047252 A1 | 5/2006 |
| WO | WO 2007/073345 A1 | 6/2007 |
| WO | WO 2009/051741 A2 | 4/2009 |
| WO | WO 2009/151632 | 12/2009 |
| WO | WO 2009/154558 A1 | 12/2009 |
| WO | WO 2011/042442 A1 | 4/2011 |
| WO | WO 2011/068764 A2 | 6/2011 |
| WO | WO 2011/099925 A1 | 8/2011 |
| WO | WO 2011/154143 A1 | 12/2011 |
| WO | WO 2013/120886 A1 | 8/2013 |
| WO | WO 2014/044823 A1 | 3/2014 |

OTHER PUBLICATIONS

Mann et al., "Dual Modality Live Cell Imaging with Multiple-Wavelength Digital Holography and Epi-Fluorescence," Topical Editor: Dr. Tristan Colomb, 3D Res.2, Accepted: Nov. 3, 2010.

Pavillon, et al., "Cell Morphology and Intracellular ionic homeostasis explored with a multimodal approach combining epifluorescene and digital holographic microscopy," Journal of Biophotonics, vol. No. 7, pp. 432-436, Accepted Mar. 5, 2010.

Beitsch et al., "Detection of carcinoma cells in the blood of breast cancer patients," The American Journal of Surgery, vol. 180, pp. 446-449 (Dec. 2000).

Boulet et al., "Cancer Epidemiology," Biomarkers & Prevention, 2008, 17(4): 810-817.

Daneshpanah et al., "3D Holographic Imaging and Trapping for Non-Invasive Cell Identification and Tracking," Journal of Display Technology, vol. 6(10), pp. 490-499 (Oct. 2010).

Fook Chiong Cheong et al. "Flow visualization and flow cytometry with holographic video microscopy", Proceedings of the SPIE—The International Society for Optical Engineering SPIE—The International Society for Optical Engineering USA, vol. 7619, 2010, XP040518833, ISSN: 0277-786X. Published Feb. 10, 2010.

Frank Dubois et al. "Applications of digital holographic microscopes with partially spatial coherence sources", Journal of Physics: Conference Series, Institute of Physics Publishing, Bristol, GB, vol. 139, No. 1, p. 12027, XP020148183, ISSN: 1742-6596. Published Nov. 1, 2008.

Fu et al., "Quantitative DIC microscopy using an off-axis self-interference approach," Optics Letters, vol. 35(14), pp. 2370-2372 (Jul. 15, 2010).

Indebetouw, G. et al. Feb. 20, 2007. Scanning holographic microscopy with resolution exceeding the Rayleigh limit of the objective by superposition of off-axis holograms. Applied Optics 46(6): 993-1000. speif. pp. 993, 994.

Kemper, B. et al. Feb. 1, 2008. Digital holographic microscopy for live cell applications and technical inspection. Applied Optics 47(4): A52-A61. specif. pp. A52, 53, 56, 59.

Kemper et al., "Monitoring of laser micro manipulated optically trapped cells by digital holographic microscopy," J Biophoton, vol. 3(7), pp. 425-431 (2010).

Kemper et al., "Investigation of living pancreas tumor cells by digital holographic microscopy," Journal of Biomedical Optics, vol. 11(3), pp. 034005-1-034005-8 (May/Jun. 2006).

Kemper et al., "Simplified approach for quantitative digital holographic phase contrast imaging of living cells," Journal of Biomedical Optics, vol. 16(2), pp. 026014-1-026014-4 (Feb. 2011).

Kemper et al., "Self interference digital holographic microscopy approach for inspection of technical and biological phase specimens," Proceedings of the SPIE—The International Society for Optical Engineering SPIE—The International Society for Optical Engineering USA, vol. 8082, May 23, 2011.

(56) References Cited

OTHER PUBLICATIONS

Kosmeier et al., "Determination of the Integral Refractive Index of Cells in Suspension by Digital Holographic Phase Contrast Microscopy", Biophotonics: Photonic Solutions for Better Health Care, Proc. of SPIE vol. 6991, 699110 (2008).

Lee et al., "Incremental feature weight learning and its application to a shape-based query system," Pattern Recognition Letters, vol. 23, pp. 865-874 (2002).

Ling et al., "Application of Flow Cytometry for Biomarker-Based Cervical Cancer Cells Detection," Diagnostic Cytopathology, vol. 36, No. 2, dated 2008.

Marin et al., "A meta-index for querying distributed moving object database servers," Information Systems, vol. 35, pp. 637-661 (2010).

Mcclatchey et al., "Object Databases in a Distributed Scientific Workflow Application," Information Technology, 1997, BIWIT '97., Proceedings of the Third Basque International Workshop on Biarritz, France, Jul. 2-4, 1997; Los Alamitos, CA, USA, IEEE Comput. Soc. US, Jul. 2, 1997, pp. 11-21.

Mihailescu M et al., "Microchannel-pinhole parameters investigation for cells visualization in holographic microscopy", Semiconductor Conference (CAS), 2011 International, IEEE pp. 75-78, XP032069149, DOI: 10.1109/SMICND.2011.6095718 ISBN: 978-1-61284-173-1. Published Oct. 17, 2011.

Moon et al., "Automated Three-Dimensional Identification and Tracking of Micro/Nanobiological Organisms by Computational Holographic Microscopy," Proceedings of the IEEE, vol. 97(6), pp. 990-1010 (Jun. 2009).

Nenadic et al., "A Possibility of Applying Differential Digital Holography in Manufacturing Process," 48th International Symposium ELMAR-2006, Jun. 7-9, 2006, Zadar, Croatia, pp. 103-106.

Owens et al., "Distinguishing Prostatic from Colorectal Adenocarcinoma on Biopsy Samples, The Role of Morphology and Immunohistochemistry," Arch Pathol Lab Med, vol. 131, pp. 599-603 (Apr. 2007).

Sahasranuddhe et al., Future Microbiol., 2011 6(9):1-25.

Sun et al., "Visualization of fast-moving cells in vivo using digital holographic video microscopy," Journal of Biomedical Optics, vol. 13(1), pp. 014007-1-014007-9 (Jan./Feb. 2008).

Reese et al., "Quantitative Analysis of Living Cells by Digital Holographic Microscopy," Biomedical Science & Engineering Conference, 2009, First Annual Ornl, IEEE, Piscataway, New Jersey, USA, pp. 1-4 (Mar. 18, 2009).

Wang et al., "Nanoscale Nuclear Architecture for Cancer Diagnosis Beyond Pathology via Spatial-Domain Low-Coherence Quantitative Phase Microscopy," Journal of Biomedical Optics, vol. 15(6), 066028, published Dec. 23, 2010.

Weigum et al., "Nano-Bio-Chip Sensor Platform for Examination of Oral Exfoliative Cytology," Cancer Prevention Research, vol. 3, pp. 518-528 (2010).

White et al., "Isolation of Stool-Derived Mucus Provides a High Yield of Colonocytes Suitable for Early Detection of Colorectal Carcinoma," Cancer Epidemiol Biomarkers Prev, vol. 8, pp. 2006-2013 (2009).

Wikipedia, "Quantitative Phase-Contrast Microscopy" retrieved from http://en.wikipedia.org/w/index.php?title=Quantitative_phase-contrast microscopy&oldid=734365574, last modified on Aug. 13, 2016.

Yeom et al., "Automatic Identification of Biological Microorganisms Using Three-Dimensional Complex Morphology," Journal of Biomedical Optics, vol. 11(2), 0124017, published Mar. 24, 2006.

Yong-Seok Choi et al., "Lateral and cross-lateral focusing of spherical particles in a square microchannel", Lab on a Chip, vol. 11, No. 3, pp. 460-465, XP55032064, ISSN: 1473-0197, DOI: 10.1039/c0lc00212g. Published Feb. 1, 2011.

Zhou et al., "An Image Clustering and Retrieval Framework Using Feedback-based Integrated Region Matching," 2009 International Conference on Machine Learning and Applications, 2009, ICMLA '09, IEEE, Piscataway, New Jersey, USA, Dec. 13, 2009, pp. 596-601.

International Search Report for Application No. PCT/EP2014/066312, dated Jan. 10, 2014, in 3 pages.

International Preliminary Report for Application No. PCT/EP2013/052852, dated May 11, 2014, in 13 pages.

International Search Report for Application No. PCT/EP2013/052852, dated Apr. 25, 2013, in 5 pages.

International Preliminary Report for Application No. PCT/EP2013/052852, dated May 13, 2014, in 13 pages.

International Search Report for Application No. PCT/EP2013/052852, dated Apr. 18, 2013, in 5 pages.

\* cited by examiner

DIGITAL HOLOGRAPHIC MICROSCOPE WITH ELECTRO FLUIDIC SYSTEM, SAID ELECTRO-FLUIDIC SYSTEM AND METHODS OF USE

TECHNICAL FIELD

The invention pertains to the technical field of analyzing and monitoring the state and the processes in a reactor or incubator, using a digital holographic microscope (DHM). More in particular, the reactor may contain a fluid medium, and can be e.g. a bio-reactor containing biological organisms such as cells, bacteria, yeasts, micro-organisms, nematodes or any combination thereof in a liquid medium.

BACKGROUND

In biology, biotechnology, chemistry and related areas such as bio-chemistry, yeasting factories, breweries . . . practical use is made of reactors, containers or incubators comprising a fluid medium, or samples which contain a fluid medium, into which certain processes occur, whereby the environmental parameters are under control. Examples are cell diagnostics and research laboratories where cell processes are to be monitored or observed, breweries such as beer breweries, where yeasting processes may have to be closely monitored, etc. Other examples are fermentators or fermentation reactors, water supply systems, plumbing, sewer systems, water canalizations, water quality improving and/or inspection installations or water purification plants, etc. where the objects in suspension are to be monitored or analyzed. To analyze and/or monitor the state and/or processes in the reactor, one has a choice between bringing the analysis apparatus to the reactor or taking samples from the reactor to the analysis apparatus. In the former case, typical problems are e.g. that the analysis apparatus needs to be resistant to the specific environment in the reactor, that the apparatus, when reused with another reactor, does not contaminate this other reactor, that the analysis apparatus is very expensive, that the apparatus is not accurate enough, etc.; in the latter case, a typical problem is the often time-consuming and/or labor-intensive gathering and preparing of samples for further observation or analysis. In such cases, it may be impossible to accurately monitor the state and/or processes of the reactor, as the time delay between the gathering of a sample and the analysis results may become too big.

Patent application US 2010/0315501 A1 discloses an electronic imaging flow-microscope for remote environmental sensing, bioreactor process monitoring, and optical microscopic tomography applications. Hereby, a fluid conduit has a port on each end of a thin flat transparent fluid transport region. A planar illumination surface contacts one flat side of the transparent fluid transport region and a planar image sensing surface contacts the other flat side. Light from the illumination surface travels through the transparent fluid transport region to the planar image sensing surface, producing a light field affected by the fluid and objects present. The planar image sensing surface creates electrical image signals responsive to the light field. The planar illumination surface can be light emitting elements such as LEDs, OLEDs, or OLET, whose illumination can be sequenced in an image formation process. The flow microscope can further comprise flow-restricting valves, pumps, energy harvesting arrangements, and power management.

However, traditional flow microscopes do not always provide enough information on the objects suspended in a flow. In some applications, three-dimensional data is to be acquired from these objects. Therefore, digital holographic imaging techniques may be applied.

Holography is a three-dimensional (3D) imaging technique that makes use of the interference between a reference wave and a wave emanating from the sample called object wave. The purpose of this interference is to record the phase of the object wave, which is related to the 3D character of the sample. With digital holographic imaging (DHI), real-time observations can be achieved by using a charged coupled device (CCD) camera as recording device and by performing a numerical reconstruction of the hologram. This idea has been proposed for the first time over 30 years ago by J. W. Goodmann, R. W. Lawrence, in "Digital image formation from electronically detected holograms," Appl. Phys. Lett, Vol. 11, 1967. As a result of technological progresses achieved in the fields of digital image acquisition and processing, this numerical or digital approach of holography has considerably extended the fields of its potential applications and different types of DHI-inspired imaging systems have been developed during the last years.

DHI techniques can be classified in two main categories: in-line techniques characterized by the fact that the reference and object waves have similar propagation directions, and off-axis techniques for which the two interfering waves propagates along different direction. The procedure for hologram formation in in-line digital holography is similar to the procedure used for phase measurements with so-called phase-shifting interferometric techniques. Hologram formation with in-line techniques requires the acquisition of several images, at least three, that must be recorded during a modulation of the reference phase. Off-axis techniques, are simpler from the experimental point of view since they require a single hologram acquisition without modulation of the phase of the reference wave. In-line techniques however present the advantage that the reconstructed images are free of twin images and zero order of diffraction. Among off-axis techniques, we can distinguish methods based on Fourier-transform holography, and methods based on a so-called Fresnel holography. With Fourier-transform methods the reference wave must be a spherical wave of precisely controlled curvature and image reconstruction is basically performed by Fourier transformation of the hologram. With Fresnel-holography based techniques, the reconstruction procedure is more sophisticated but more flexibility is offered to build experimental installations.

Among recent publications presenting developments or applications of DHI-inspired techniques, we can mention the following works. A study of some general performances of an in-line technique is presented in "Image formation in phase-shifting digital holography and application to microscopy", 1. Yamaguchi et al., Applied Optics, Vol. 40, No. 34, 2001, pp. 6177-6186. In "Fourier-transform holographic microscope", Applied Optics, Vol. 31, 1992, pp. 4973-4978, W. S. Haddad et al describe the general principle of Fourier-transform DHI.

Examples of applications of the Fresnel-based approach can be found in "Direct recording of holograms by a CCD target and numerical reconstruction", U. Schnars and W. Juptner, Applied Optics, Vol. 33, 1994, pp. 179-181, and in "Performances of endoscopic holography with a multicore optical fiber", O. Coquoz et al., Applied Optics, Vol. 34, 1995, pp. 7186-7193.

A key element of a DHI method is the numerical method used for hologram reconstruction. An original reconstruction procedure, which allows for reconstructing simultaneously the amplitude and the phase of the object wave, on the basis of a single off-axis hologram acquisition, has been developed by Cuche et al. and is presented in U.S. Pat. No. 6,262,218, and in WO 00/20929. Different applications and implementations of this technique are presented in "Digital holography for quantitative phase-contrast imaging", Optics Letters, Vol. 24, 1999, pp. 291-293, in "Simultaneous amplitude-contrast and quantitative phase-contrast microscopy by numerical reconstruction of Fresnel off-axis holograms", Applied Optics, Vol. 38, 1999, pp. 6994-7001, in "Spatial Filtering for Zero-Order and Twin-Image Elimination in Digital Off-Axis Holography", Applied Optics, Vol. 38 No. 34, 1999, in "Aperture apodization using cubic spline interpolation: Application in digital holographic microscopy", Optics Communications, Vol. 182, 2000, pp. 59-69, and in "Polarization Imaging by Use of Digital Holography", T. Colomb et al., Applied Optics, Vol. 38, No 34, 1999.

DHI method presents interesting possibilities of applications in cell biology. Indeed a living cell behaves optically as a phase object, i.e. a transparent sample whose constituents can be optically probed on the basis of the phase shift they induce on the light crossing them.

The phase-shifting behavior of transparent sample is well known, and for a long time as it constitutes the mechanism of image formation in phase-contrast (PhC) and Nomarski (DIC) microscopy. Even though these two techniques are widely used in biological microscopy, and well suited as contrasting methods, they cannot be used for precise quantitative phase measurements. The DHI method instead, is reminiscent of classical interferometry, which is the most commonly used technique for phase measurements. However, whereas interferometric techniques are widely used in metrology, only few biological applications have been reported, by R. Barer and S. Joseph, in "Refractometry of living cells", Quarterly Journal of Microscopical Science, Vol. 95, 1954, pp. 399-423, by R. Barer in "Refractometry and interferometry of living cells", Journal of the Optical Society of America, Vol. 47, 1957, pp. 545-556, by A. J. Coble et al. in "Microscope interferometry of necturus gallblader epithelium", Josiah Macy Jr. Fundation, New York, 1982, p. 270-303, by K. C. Svoboda et al. in "Direct observation of kinesin stepping by optical trapping interferometry", Nature, Vol. 365, 1993, by J. Farinas and A. S. Verkman, in "Cell volume plasma membrane osmotic water permeability in epithelial cell layers measured by interferometry", Biophysical Journal, Vol. 71, 1996, pp. 3511-3522, by G. A. Dunn and D. Zicha in "Dynamics of fibroblast spreading", Journal of Cell Science, Vol. 108, 1995, pp. 1239-1249.

For biological applications, as well as for material science or metrology applications, DHI methods offer a novel alternative to classical interferometry with similar performances but simplified experimental procedures. The main advantage originates from the fact that complex and costly experimental optical devices can be handled by digital processing methods. For example, as described by E. Cuche et al. in "Simultaneous amplitude-contrast and quantitative phase-contrast microscopy by numerical reconstruction of Fresnel off-axis holograms", Applied Optics, Vol. 38, 1999, pp. 6994-7001, the wave front deformations appearing when a microscope objective is introduced along the path of the object wave can be compensated using a digital procedure. This particular feature opens attractive possibilities in the fields of microscopy. In addition DHI techniques performs faster than interferometric techniques, and provides more information about the sample, in particular, the amplitude and the phase of the object wave can be obtained simultaneously on the basis of a single hologram acquisition.

DHI methods have been applied to static imaging of biological cells, without phase reconstruction by K. Boyer et al. in "Biomedical three-dimensional holographic microimaging at visible, ultraviolet and X-ray wavelength", Nature Medicine, Vol. 2, 1996, pp. 939-941, and by F. Dubois et al. in "Improved three-dimensional imaging with a digital holography microscope with a source of partial spatial coherence", Applied Optics, Vol. 38, 1999, pp. 7085-7094. DHI of cells using a phase measurement modality requiring several image acquisitions has been reported by G. Indebetouw and P. Klysubun in "Saptiotemporal digital microholography", Journal of the Optical Society of America A, Vol. 18, 2001, pp. 319-325.

With DHI, image acquisition can be performed at video-rate, and even faster using appropriate image acquisition systems, for experimental periods of up to several hours. Due to its interferometric nature, DHI has a high axial resolution (nanometer scale), which allows for observing subtle and minute modifications of sample shape, opening a wide field of applications in both life and material sciences. With the event of video-rate image acquisition by DHI, it has become possible to use DHI with a flow microscope, even at high flow rates.

WO2003048868 discloses an apparatus and a method for performing digital holographic imaging of a sample which includes a holographic creation unit, a holographic reconstruction unit, a processing unit, and a sample unit. The sample unit includes a container that contains a medium in which a sample is located.

U.S. Pat. No. 7,463,366 discloses a method and device for obtaining a sample with three-dimensional microscopy, in particular a thick biological sample and the fluorescence field emitted by the sample. One embodiment includes obtaining interferometric signals of a specimen, obtaining fluorescence signals emanating from the specimen, recording these signals, and processing these signals so as to reconstruct three-dimensional images of the specimen and of the field of fluorescence emitted by the specimen at a given time. Another embodiment includes a digital holography microscope, a fluorescence excitation source illuminating a specimen, where the microscope and the fluorescence excitation source cooperate to obtain interferometric signals of the specimen and obtain fluorescence signals emanating from the specimen, means for recording the interferometric signals and fluorescence signals, and means for processing the interferometric signals and the fluorescence signals so as to reconstruct three-dimensional images of the specimen and of the field of fluorescence emitted by the specimen at a given time.

Patent application WO2004102111 discloses a compact microscope able to work in digital holography for obtaining high quality 3D images of samples, including fluorescent samples and relatively thick samples such as biological samples, said microscope comprising illumination means at least partially spatially coherent for illuminating a sample to be studied and a differential interferometer for generating interfering beams from said sample on the sensor of an electronic imaging device, said interferometer comprising namely tilting means for tilting by a defined angle one the interfering beams relatively to the other, said tilting resulting into a defined shift of said interfering beam on the sensor of the electronic imaging device, said shift being smaller than spatial coherence width of each beam, said microscope being able to be quasi totally preadjusted independently from the samples so that minimum additional adjustments are required for obtaining reliable 3D images of samples.

However, the above mentioned prior art DHI techniques do not disclose how one can obtain data from an extensive sample of objects suspended in a fluid, nor the possibility of obtaining such data within a relatively short period. More in particular, most prior art DHI techniques focus on the imaging of small samples contained within a small specimen, whereby the accuracy and 3D imaging of DHI is being exploited, rather than its high rate of obtaining 3D information.

The problems in the prior art are multiple. The data acquired with the analysis apparatus of the prior may not be accurate enough, it may not be obtained quickly enough, the apparatus may be too expensive, it may only give two-dimensional and/or analogue images whereby three-dimensional information is obtained only after e.g. making a set of 2D images, digitalization and performing a CT-processing step. More in particular, DHMs may provide images and/or directly digitalized information about samples which is superior to other imaging or analysis techniques, but can be rather expensive. Furthermore, the gathered sample may need to be processed before analysis, which can be a time-consuming and labor-intensive procedure. Contamination may be an issue when the same apparatus is used to monitor or analyze different reactors, or the same reactor at different positions of times. Prior art techniques may not always provide the possibility of returning the sample to the reactor or to another reactor, or the possibility of real-time monitoring and providing timely feedback for adapting the reactor's environmental parameters.

Furthermore, it is not always practical to connect or disconnect a reactor to a monitoring system. Also, when installing a monitoring system for monitoring and/or observing and/or analysis of a reactor, a lot of manual handling is usually performed, leaving room for errors during installation. Furthermore, because of the high amount of manual handling, substantial time loss can occur in situations where a lot of installations need to be performed, e.g. in laboratories for research or large-scale analysis of multiple samples.

There remains a need in the art for an improved system for the monitoring and/or analysis of one or more reactors and/or incubators comprising a fluid medium or comprising sample containing a fluid medium, in particular biological or biochemical cultures of organisms such as cells, bacteria, yeasts, micro-organisms, nematodes or any combination thereof, preferably in a liquid.

The present invention aims to resolve at least some of the problems mentioned above.

The invention thereto aims to provide an improved system for the monitoring and/or analysis of one or more reactors and/or incubators comprising a digital holographic microscope (DHM) and one or more electro-fluidic systems which are capable of guiding a sample of the contents of a reactor with a fluid medium to the DHM for analysis and preferably back to the reactor. As such, one DHM can serve to analyze or monitor multiple reactors, and/or one reactor at different positions, e.g. at different heights, or at different times. The electro-fluidic systems may be arranged such that contamination is avoided and replacement and installation is easy and less likely subject to errors.

SUMMARY OF THE INVENTION

The present invention concerns a fluid microscope system for analyzing and/or monitoring the contents of one or more fluid-based reactors or canalizations such as bio-reactors, micro-reactors, brewing reactors, water supply systems or sewer systems, comprising:
  a. a digital holographic microscope (DHM) capable of obtaining phase information of a fluid sample and comprising illumination means;
  b. one or more electro-fluidic systems suitable for connection to said reactors and to said DHM, for guiding fluid from said reactors to said DHM, whereby each electro-fluidic system comprises one or more tubes, whereby said tubes comprise a first connector at a proximal end of the tubes suitable for being operatively received in the DHM and a second connector at a distal end of the tubes suitable for being operatively connected to one of said reactors, and whereby said tubes are suitable for coming in direct contact with fluid from said reactor and whereby said tubes comprise a part which has a shape suitable for said DHM and is at least partially transparent for the illumination means of said DHM for obtaining holographic information of said fluid sample;

characterized in that each of said electro-fluidic systems comprises at least one pumping system, operatively coupled to said tubes for inducing fluid flow in said tubes, and one, two or more electrical conductors, running at least partially along said tubes and attached thereto, whereby said electrical conductors are suitable for providing electrical signals and/or electrical power to said pumping system and whereby a first end of said electrical conductors is attached to the first connector, and a second end to the pumping system.

By comprising electrical conductors that can provide electrical signals and/or power to the pumping system, the pumping system can be controlled by a controller unit in or near the DHM. In a preferred embodiment, said controller unit is comprised in the DHM. This would make use and installation of the system more efficient by being able to control flow from the DHM where the observations are made, instead of having to operate the pump directly or through a separate device.

In a preferred embodiment, an electro-fluidic system will comprise two tubes, sharing a first connector at the proximal end suitable for being operatively received in the DHM, each tube having a second connector at the distal end suitable for being operatively connected to a reactor. The part of the tubes which is at least partially transparent for the illumination means of the DHM will be arranged to allow fluid connection between the proximal ends of the tubes and will be located near to said first connector. This can also be perceived as being only one tube. By sharing the first connector, attaching an electro-fluidic system to the DHM will require less manual handling and will make for less loose tubes and thereby a more user-friendly system. It will also allow fluid flow from a first reactor to a DHM to a second reactor.

In a further preferred embodiment, the present invention provides a fluid microscope system, having an electro-fluidic system which will comprise two tubes, sharing a first connector at the proximal end of the tubes suitable for being operatively received in the DHM, and sharing a second connector at the distal end of the tubes suitable for being operatively connected to a reactor. The part of the tubes which is at least partially transparent for the illumination means of the DHM will be arranged to allow fluid connection between the proximal ends of the tubes and will be located near to said first connector. By sharing both connectors, this will further reduce the number of wires, require less manual handling and make for a more user-friendly system.

In a further preferred embodiment, the present invention provides a system, having an electro-fluidic system which will comprise two electrical conductors, running along at least one of said tubes. The proximal end of said two conductors is attached to the first connector, the distal end of said two conductors is connected to the pumping system, and adapted to transmit electrical signals and/or power from a controller to which it is coupled through the first connector to the pumping system.

In a preferred embodiment, the electro-fluid system comprises mounting means for mounting a pumping system onto said one or more tubes to induce a fluid flow, and optionally a pump system, arranged to be mounted on the mounting means and arranged for inducing fluid flow in said tubes, whereby two electrical conductors of said electro-fluidic system are connected with a first end to the first connector and with a second end to the mounting means for transmitting electrical signals and/or electrical power to a device mounted on said mounting means.

In a preferred embodiment, the present invention provides a system as described above, whereby the pumping system comprises a stepwise pump, capable of inducing a stepwise fluid flow in an electro-fluidic system to which said stepwise pump is connected, and optionally a valve system. Said stepwise pump supplies samples for observation to the DHM through the electro-fluidic system at regular intervals, thereby allowing the DHM to observe, process and analyze the data from a sample, before being supplied a next sample. Said stepwise pump is most preferably a diaphragm pump. By combining the valve system with a diaphragm pump, it is ensured that the fluid in the tubes is pumped in the correct direction.

The preferred use of a diaphragm pump is due to sterility reasons. A diaphragm or membrane pump does not put the fluid to be observed in direct contact with elements that might contaminate said fluid, as is the case with certain other types, such as plunger pumps or piston pumps, where moving elements of the pumps can track pollutants into the fluid they are to move. Furthermore, diaphragm pumps are well suited for handling highly viscous liquids, even when containing grit and solid content, they work very efficiently and can resist high discharge pressures.

In an alternatively preferred embodiment, the present invention provides a system as described above, whereby the pumping system comprises a continuous pump, capable of inducing a continuous fluid flow in an electro-fluidic system to which said continuous pump is connected, and optionally a valve system. Said continuous pump is capable of supplying a continuous fluid flow to the DHM, which may result in a higher throughput and therefore a faster analysis or better monitoring of the processes in the reactor and electro-fluidic system. Furthermore, due to its fast acquisition time, a DHM is capable of acquiring high-quality holographic images of a sample, even if a continuous flow is present in said sample. In a more preferred embodiment, said pump is a diaphragm pump. This instrument has been described in the prior art, for instance in U.S. Pat. No. 5,482,447.

In a preferred embodiment, the present invention provides a system as described above, whereby said tubes comprise a part which is at least partially transparent for the illumination means of said DHM and which has a shape suitable for said DHM. This partially transparent part will preferably be located at or near the first connector and adapted to provide optical contact between the illumination means of the DHM and the fluid sample in the partially transparent part.

In a preferred embodiment, the present invention provides a system as described above, whereby said tube has a part comprising two parallel transparent sides and whereby said DHM is capable of working in transmission mode.

In a preferred embodiment, the present invention provides a system as described above, whereby said part comprises at least one transparent side and whereby said DHM is capable of working in reflection mode.

In a preferred embodiment, the present invention provides a system as described above, whereby said part comprises a flow cell and/or microfluidic system.

In a preferred embodiment, the electro-fluidic system comprises a second connector at the distal end of the tubes which is provided with a reactor attachment system for easily attaching and/or detaching tubes of the electro-fluidic system to and/or from a reactor, whereby leakage of fluid is prevented. By attaching the tubes to the reactor, a fluid connection is established between the tubes and the reactor.

In a second aspect, the present invention provides an electro-fluidic system for a fluid microscope system for analyzing and/or monitoring the contents of one or more fluid-based reactors or canalizations, comprising:
a. one or more tubes for guiding a fluid flow between the DHM and the reactors of said system, whereby said one or more tubes are suitable for coming in direct contact with fluid from said reactors and comprise:
  i. a first connector at a proximal end of the tubes, suitable for being operatively received in the DHM, and a second connector at a distal end of the tubes, suitable for being operatively connected to one of said reactors;
  ii. and a part which is at least partially transparent for the illumination means of said DHM for obtaining holographic information of said fluid sample;
b. mounting means for mounting a pumping system onto said one or more tubes to induce a fluid flow;
c. optionally a pump system, arranged to be mounted on the mounting means and arranged for inducing fluid flow in said tubes, characterized in that said electro-fluidic system comprises one, two or more electrical conductors for transmitting electrical signals and/or electrical power to a device mounted on said mounting means, whereby said electrical conductors are arranged and attached at least partially along one of said tubes, and whereby a first end of said conductors is attached to the first connector, and a second end to the mounting means. The part of the one or more tubes which is at least partially transparent for the illumination means of the DHM, has a shape suitable for said DHM.

In a preferred embodiment, said mounting means is attached to said tubes towards the distal end. By locating the mounting means on the distal end of the tubes, the pump system will be placed near to the reactor. This will facilitate the operation of the pump, as the closer it is to the reactor from which it is to draw the fluid, the more effective it will be able to function, especially when the pressure in the reactor is low. The inclusion of electrical conductors in the electro-fluidic system allows, as mentioned above, for a pump system to be attached to said system and controlled from a controller in or near the DHM, without requiring manual operation of the pumping system or a separate system.

In a preferred embodiment, the electro-fluidic system will comprise two tubes, sharing a first connector at the proximal end suitable for being operatively received in the DHM, each tube having a second connector at the distal end suitable for being operatively connected to a reactor. The part of the tubes which is at least partially transparent for the illumination means of the DHM is arranged to allow fluid connection between the proximal ends of the tubes and is located at or near said first connector. This can also be perceived as being only one tube. The partially transparent part is preferably located near the first connector as, when the electro-fluidic system is operatively coupled to the DHM by introducing the first connector into said DHM, the partially transparent part should be arranged to be near the illumination means of the DHM.

In a further preferred embodiment, the present invention provides an electro-fluidic system which comprises two tubes, sharing a first connector at the proximal end of the tubes suitable for being operatively received in the DHM, and sharing a second connector at the distal end of the tubes suitable for being operatively connected to a reactor. The part of the tubes which is at least partially transparent for the illumination means of the DHM is preferably arranged to allow fluid connection between the proximal ends of the tubes and is located at or near said first connector.

In a further preferred embodiment, the present invention provides an electro-fluidic system which comprises two electrical conductors, running along one of said two tubes. A proximal end of said two conductors is attached to the first connector, a distal end of said two conductors is connected to the mounting means for mounting a pumping system, and adapted to transmit electrical signals and/or power from a controller to which it is coupled through the first connector to a pumping system which is or can be operatively attached to the mounting means.

In a preferred embodiment, the present invention provides an electro-fluidic system as described above, whereby at least one tube of said electro-fluidic system comprises a fluid-tight flexible part which, when compressed, pulled and/or pushed, results in a fluid flow in said tube. The pumping system can hence provide a fluid flow in the tubes by moving the flexible part. This flexible part can be a membrane suitable for being compressed and decompressed by a diaphragm pump to provide a fluid flow in the tubes.

In a preferred embodiment, the present invention provides an electro-fluidic system as described above, whereby the pumping system comprises a diaphragm pump and a valve system. In combination with the diaphragm pump, the valve system will only allow fluid flow in one direction, thus eliminating danger of contaminating the reactor with backflow. The diaphragm pump actuates on the fluid-tight flexible part of the tubes and, by compressing and/or decompressing said flexible part, provides a fluid flow in the tubes.

In a preferred embodiment, the present invention provides an electro-fluidic system as described above, said electro-fluidic system forms a closed fluidic circuit for flow of fluid medium between one of said reactors and said DHM and back to said reactor when the electro-fluidic system is operatively attached to said reactor and said DHM. The coupling will be executed by introducing the first connector of the tubes into the DHM and connecting the second connector of the tubes to the reactor.

In a preferred embodiment, the present invention provides an electro-fluidic system as described above, whereby the electrical conductors form a closed electrical circuit for transmitting electrical signals and/or power, between a controller and a pumping system when the electrical conductors are operatively attached to said controller and the pumping system is mounted on the mounting means of the electro-fluidic system. The electrical conductors are connected to the mounting means.

In a further preferred embodiment, said controller is part of the DHM.

In a preferred embodiment, the present invention provides an electro-fluidic system as described above, whereby said electro-fluidic system comprises a pumping system arranged for inducing fluid flow in one or more tubes of said electro-fluidic system and arranged for receiving control signals and/or power from a controller through an electrical connection by the electrical conductors from said controller to the pumping system. In the current embodiment, the mounting means of the electro-fluidic systems is connected to the electrical conductors. By mounting the pumping system on the mounting means, the pumping system is automatically and correctly connected to the electrical conductors and thereby electrically connected the controller.

At least one pumping system may comprise a stepwise pump, capable of inducing a stepwise fluid flow in an electro-fluidic system to which said stepwise pump is connected, and/or at least one pumping system may comprise a continuous pump, capable of inducing a continuous fluid flow in an electro-fluidic system to which said continuous pump is connected. In a more preferred embodiment, said pump is a diaphragm pump. In an alternative embodiment, said pump is a peristaltic pump.

In a preferred embodiment, the present invention provides an electro-fluidic system as described above, whereby the pumping system is permanently mounted on the mounting means of the electro-fluidic system.

In an alternative embodiment, the present invention provides an electro-fluidic system as described above, whereby the pumping system is removably mounted on the mounting means of the electro-fluidic system.

In a preferred embodiment, the present invention provides an electro-fluidic system as described above, whereby the pumping system comprises a power source and can be powered by said power source. Preferably said power source comprises a battery, such as a rechargeable battery.

In a further preferred embodiment, said power source is removable with respect to the pumping system and/or the electro-fluidic system.

In a preferred embodiment, the present invention provides an electro-fluidic system as described above, said electro-fluidic system comprises a sheathing for protecting said electro-fluidic system, whereby said sheathing encloses the tubes and the associated electrical conductors of said electro-fluidic system.

In a preferred embodiment, the present invention comprises a sheathing for an electro-fluidic system as described above, preferably whereby said tubes and the associated electrical conductors are sterile.

In a third aspect, the present invention provides a method for installing an electro-fluidic system as described above, in a fluid microscope system as described above, comprising the following steps:

a) operatively coupling said electro-fluidic system to said reactor or canalization by connecting the second connectors of one or more tubes to said reactor or canalization;

b) operatively coupling said electro-fluidic system to a DHM of said fluid microscope system by connecting the first connectors of said one or more tubes to said DHM; and c) operatively coupling a pumping system to said electro-fluidic system by mounting said pumping system on the mounting means of the electro-fluidic system.

This facilitates the installation of an electro-fluidic system, as it involves less manual handling and a clear way of mounting a pumping system. Furthermore, the electro-fluidic system is arranged in such a way that manual connection errors of the electrical conductors and/or the tubes with either DHM or reactor are avoided.

In a preferred embodiment, an electro-fluidic system will comprise two tubes, sharing a first connector and sharing a second connector. Operatively coupling the electro-fluidic system to a reactor or canalization requires connecting the second connector to the reactor or canalization. Operatively coupling the electro-fluidic system to a DHM requires introducing the first connector into the DHM.

In a fourth aspect, the present invention provides a method for replacing an electro-fluidic system as described above, in a fluid microscope system as described above, comprising the following steps:
  a. removing said electro-fluidic system from operative coupling with a DHM of said fluid microscope system;
  b. removing said electro-fluidic system from operative coupling with said one or more fluid-based reactors or canalizations;
  c. operatively coupling a replacement electro-fluidic system to one of said reactors or canalizations by connecting the second connectors of one or more tubes of the replacement electro-fluidic system to said one reactor or canalization;
  d. operatively coupling said replacement electro-fluidic system to a DHM of said fluid microscope system by introducing the first connectors of said one or more tubes of the replacement electro-fluidic system into said DHM;
  b. and operatively coupling a pumping system to said replacement electro-fluidic system by mounting said pumping system on the mounting means.

In a preferred embodiment, an electro-fluidic system will comprise two tubes, sharing a first connector and sharing a second connector. Operatively coupling or removing the electro-fluidic system to or from a reactor or canalization requires connecting or disconnecting the second connector to or from the reactor or canalization. Operatively coupling or removing the electro-fluidic system to a DHM requires introducing or removing the first connector into or from the DHM.

In a fifth aspect, the present invention provides a method for observing and/or monitoring suspended objects in a fluid in a fluid-based reactor or canalization, comprising following steps:
  d) inducing a fluid flow by a pumping system from said reactor or canalization to a DHM;
  e) capturing a sample and observing said sample with the DHM;
  f) optionally inducing a fluid flow from said DHM to said reactor or canalization and optionally returning the sample to the fluid flow,
characterized in that the pumping system is controlled and optionally powered by said DHM.

By controlling the pumping system with the DHM, an operator can set certain parameters such as a desired fluid flow rate, a sampling time and others, thus automating the sampling process. Furthermore, by allowing control through the DHM, operators will have a central operating station and will not waste time moving to the control unit of the pumping station or pumping station itself, even more when a single DHM is used to observe or monitor several reactors or canalizations.

In a preferred embodiment, said method uses a fluid microscope system and/or electro-fluidic system as described above.

DETAILED DESCRIPTION OF THE INVENTION

Figure 1:
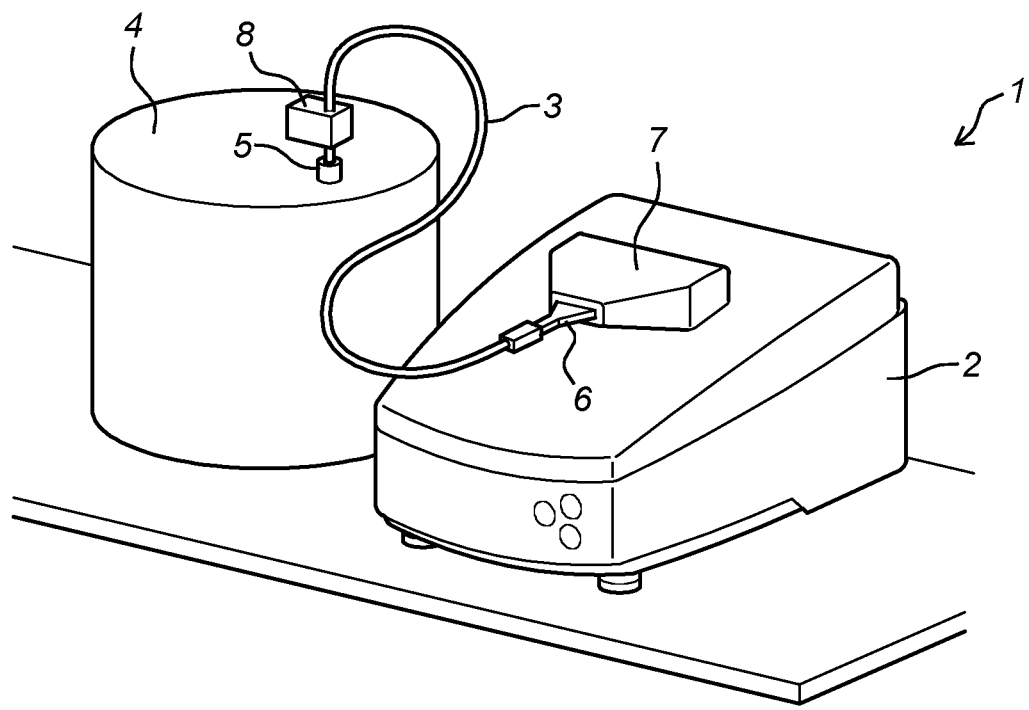
FIG. 1 shows an electro-fluidic system (3) suitable for connection to a DHM (2) and to a fluid-based reactor (4) and for guiding fluid from said reactor to the DHM (2) and back.

The present invention concerns a fluid microscope system and an electro-fluidic system according to the claims, as well as methods for installing and removing said systems and analysing and/or monitoring the contents of one or more fluid-based reactors with said systems.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The term "reactor" as used herein refers to a container or a canalization system capable of holding and/or guiding a fluid wherein objects or processes of interest are present. As such, the terms "reactor", "incubator", "container", "bioreactor", etc. are assumed to be synonyms unless the context dictates otherwise. Examples of reactors can be fermentation reactors, water supply piping or plumbing, water canalization systems, water purification reactors, brewing reactors, micro-reactors, etc.

The expression "online monitoring of a reactor", here and throughout the description unless otherwise defined, refers to monitoring when the reactor is online, i.e. when reactions are taking place or should be taking place in the reactor.

The expression "inline monitoring of a reactor", here and throughout the description unless otherwise defined, refers to monitoring inside a circuit, i.e. the content which is to be monitored is following a circuit and the monitoring occurs at a certain position in this circuit.

The expression "in situ monitoring of a reactor", here and throughout the description unless otherwise defined, refers to monitoring inside the reactor.

The expression "real-time monitoring of a reactor", here and throughout the description unless otherwise defined, refers to the monitoring of processes in the reactor at time intervals which are smaller than or of the same magnitude as the typical time of the monitored processes or inversely proportional to the process rate. This may allow for a monitoring of different stages of a process or of different stages of the content of the reactor in time; furthermore, this may allow for actions to be taken directly or almost directly after a specific process or stage has been observed in the reactor.

The term "fluid" as used herein refers to the known state of matter which continually deforms or flows under an applied shear stress. In practice, fluids are liquids, gasses or vapors, a combination of one or more liquids and/or gasses, all of which may contain objects such as solid particles, organisms such as cells, bacteria, yeasts, micro-organisms, nematodes or any combination thereof, contamination, etc. in solution, suspension or other type of mixture. Preferably, in the present invention disclosure, a fluid is in the liquid state, such as a liquid, a liquid mixture, a solution, a suspension, an emulsion, etc.

The terms "sample" and "fluid sample" as used herein is to be understood as a sample of the contents of a reactor containing specimens in a fluid state. Preferably, the fluid state is a liquid state and the sample is a liquid sample. Samples may be any specimen obtained from a chemical reaction, such as a catalytic reaction, a soil specimen, a specimen comprising micro-organisms and/or insects, a forensic specimen or a specimen from a crime scene, such as, but not limited to a hair specimen, body fluids, a water specimen, an entomological specimen, a biological specimen comprising organisms such as cells, bacteria, yeasts, micro-organisms, nematodes or any combination thereof, etc., which may be put into a fluid state if necessary, e.g. by dissolving, by suspending, by mixing, . . .

In a first aspect, the invention provides a fluid microscope system for analyzing and/or monitoring the contents of one or more fluid-based reactors or canalizations such as bioreactors, micro-reactors, brewing reactors, water supply systems or sewer systems, according to claim 1.

Using a DHM for analyzing and/or monitoring the state of and reactions in a reactor offers many advantages as compared to other analyzing/monitoring techniques, such as:
  a) the possibility of inline 3D/4D monitoring instead of the work-intensive method of collecting or hand-collecting samples at specific moments and from specific reactors and subsequent analysis on (2D/3D) microscopic systems such as traditional microscopes, phase contrast microscopes or confocal microscopes;
  b) the greater amount of information about a sample gathered in a shorter period of time compared to other microscopic techniques;
  c) the possibility of automated digitalization and even automated qualification and quantification of the sample, etc.

DHM offers directly digitalized phase information which allows 3D imaging. This is faster than other 3D imaging techniques such as CT scans which first obtain a large set of 2D images from which a 3D image is reconstructed, possibly after an extra digitalization step. Therefore, the present invention leads to a faster, more accurate and more reliable analyzing and/or monitoring of reactors by using DHM as an observation, analysis and/or monitoring apparatus or mechanism. DHM is also more apt than other microscopy system for analyzing fluid, more preferably liquid, samples, especially for obtaining 3D information, because it is faster and more accurate than e.g. CT techniques.

Digital Holographic Microscopy (DHM) is a technique which allows a recording of a 3D sample or object without the need of scanning the sample layer-by-layer. In this respect DHM is a superior technique to confocal microscopy. In DHM, a holographic representation is recorded by a digital camera such as a CCD- or a CMOS-camera, which can subsequently be stored or processed on a computer.

To make a holographic representation, or hologram, traditionally a highly coherent light source such as laser-light, is used to illuminate the sample. In the most basic set-up, the light form the source is split into two beams, an object beam and a reference beam. The object beam is sent via an optical system to the sample and interacts with it, thereby altering the phase and amplitude of the light depending on the object's optical properties and 3D shape. The object beam which has been reflected on or transmitted through the sample, is then made (e.g. by set of mirrors and/or beam splitters) to interfere with the reference beam, resulting in an interference pattern which is digitally recorded. Since the hologram is more accurate when object beam and reference beam have comparable amplitude, an absorptive element can be introduced in the reference beam which decreases its amplitude to the level of the object beam, but does not alter the phase of the reference beam or at most changes the phase globally, i.e. not dependent on where and how the reference beam passes through the absorptive element. The recorded interference pattern contains information on the phase and amplitude changes which depend on the object's optical properties and 3D shape.

An alternative way of making a hologram is by using the in-line holographic technique. In-line DHM is similar to the more traditional DHM, but does not split the beam, at least not by a beam splitter or other external optical element. In-line DHM is most preferably used to look at a not-too-dense solution of particles, e.g. cells, in a fluid. Thereby some part of the at least partially coherent light will pass through the sample without interacting with the particles (reference beam) and interfere with light that has interacted with the particles (object beam), giving rise to an interference pattern which is recorded digitally and processed. In-line DHM is used in transmission mode, it needs light with a relatively large coherence length, and cannot be used if the samples are too thick or dense.

Another DHM technique called differential DHM (DDHM) is disclosed in European patent EP 1 631 788. DDHM is different to the other techniques in that it does not really make use of reference and object beams. In a preferred set-up of DDHM, the sample is illuminated by illumination means which consist of at least partially coherent light in reflection or in transmission mode. The reflected or transmitted sample beam can be sent through an objective lens and subsequently split in two by a beam splitter and sent along different paths in a differential interferometer, e.g. of the Michelson or Mach-Zehnder type. In one of the paths, a beam-bending element or tilting means is inserted, e.g. a transparent wedge. The two beams are then made to interfere with each other in the focal plane of a focusing lens and the interference pattern in this focal plane is recorded digitally and stored by e.g. a CCD-camera connected to a computer. Hereby, due to the beam-bending element, the two beams are slightly shifted in a controlled way and the interference pattern depends on the amount of shifting. Then the beam-bending element is turned, thereby altering the amount of shifting. The new interference pattern is also recorded. This can be done a number N of times, and from these N interference patterns, the gradient (or spatial derivative) of the phase in the focal plane of the focusing lens can be approximately computed. This is called the phase-stepping method, but other methods of obtaining the phase gradient are also known, such as a Fourier transform data processing technique. The gradient of the phase can be integrated to give the phase as a function of position. The amplitude of the light as a function of position can be computed from the possibly but not necessarily weighted average of the amplitudes of the N recorded interference patterns. Since phase and amplitude are thus known, the same information is obtained as in a direct holographic method (using a reference and an object beam), and a subsequent 3D reconstruction of the object can be performed.

The use of DHM in a diagnostic setting has many advantages which makes it the ideal technique to implement in a setting such as in the current invention. Besides a bright field image, a phase shift image is created as well. The phase shift image is unique for DHM and gives quantifiable information about optical distance. In reflection DHM, the phase shift image forms a topography image of the object.

Transparent objects, like living biological organisms such as cells, bacteria, yeasts, micro-organisms, nematodes or any combination thereof, are traditionally viewed in a phase contrast microscope or in a differential interference contrast microscope. These methods visualize phase shifting transparent objects by distorting the bright field image with phase shift information. Instead of distorting the bright field image, transmission DHM creates a separate phase shift image showing the optical thickness of the object. This can also be achieved with a DHM working in reflection mode for both transparent as opaque objects. Digital holographic microscopy thus makes it possible to visualize and quantify transparent and/or opaque objects and is therefore also referred to as quantitative phase contrast microscopy. More so, DHM allows imaging subcellular structures in three dimensions.

An object image is calculated at a given focal distance. However, as the recorded hologram contains all the necessary object wave front information, it is possible to calculate the object at any focal plane by changing the focal distance parameter in the reconstruction algorithm. In fact, the hologram contains all the information needed to calculate a complete image stack. In a DHM system, where the object wave front is recorded from multiple angles, it is possible to fully characterize the optical characteristics of the object and create tomography images of the object.

Furthermore, as DHM systems do not have an image forming lens, traditional optical aberrations do not apply to DHM. Optical aberrations are "corrected" by design of the reconstruction algorithm. A reconstruction algorithm that truly models the optical setup will not suffer from optical aberrations. In optical microscopy systems, optical aberrations are traditionally corrected by combining lenses into a complex and costly image forming microscope objective. Furthermore, the narrow focal depth at high magnifications requires precision mechanics. Lastly, the needed components for a DHM system are inexpensive optics and semiconductor components, such as a laser diode and an image sensor. The low component cost in combination with the auto focusing capabilities of DHM, make it possible to manufacture DHM systems for a very low cost. Nevertheless, the cost of a DHM may still be too high for monitoring a large amount of reactors. For this, the present invention provides a system comprising one DHM and a set of electro-fluidic circuits which are capable of guiding fluid samples from multiple reactors to the DHM and preferably back. Hereby, only one DHM is needed to monitor multiple reactors and the overall cost can be reduced.

Generally, a DHM comprises illumination means which comprises a coherent light source or an at least partially coherent light source such as a LASER or LED, an interferometer which may comprise a set of mirrors and/or beam splitters, and digital recording means such as a CCD or CMOS camera and e.g. a flash card or magnetic recording device connected to it for long-time storage. A DHM may also comprise further optical components such as lenses, mirrors, prisms, attenuators, etc. Possibly, a DHM may comprise or may be connected to processing means such as a mainframe, a PC, a logical device such as a PLC, etc. A DHM may work in transmission and/or reflection mode, preferably depending on the nature of the sample which is to be observed. A DHM as used in the system of the present invention may be a traditional DHM, an in-line DHM, a differential DHM, or another kind of DHM.

However, DHM may be expensive to use for inline, in-situ, online and/or real-time analyzing and/or monitoring of the state and processes in reactors. In a laboratory with many reactors, it would be expensive to have one DHM per reactor for monitoring and analysis. The present invention solves this problem by providing one or more electro-fluidic systems which may connect the contents of the reactor to a central DHM-unit. Thereby, one DHM may be used in combination with different reactors or with one reactor whereby information about the reaction process and state is required at different positions in the reactor or at different times.

The use of a DHM in a fluid microscope system according to the present invention has the further advantage that many characteristics of the objects in the fluid medium can be automatically detected by digital holograms obtained by the DHM, and that the DHM can, on the basis of these characteristics, decide to decrease or increase e.g. the pumping speed or flow rate of the pumping system, i.e. automated control of the flow rate becomes possible. Such a control could be used to ensure the optimal flow rate for e.g. obtaining pre-defined characteristics or obtaining a high monitoring rate.

Sample collection and introduction of said samples in the observing means can be a strenuous process when done manually, as it requires accuracy, concentration and time and is a liability for human error. In some articles in the prior art, a pumping system to induce and control flow through tubes of a system that provide samples from the reactors to the DHM, is included that can either be manually or electronically operated. This is described in patent application WO 2014 044 823, where a digital holographic microscope system comprising a pumping system is claimed. A pumping system that is manually controlled is often disadvantageous as it requires a skilled person to operate the pump where it is placed, again making human error a real danger, aside from the inefficiency and possible inaccuracy of performing this process manually. A pumping system that is electronically controlled needs to be powered and operated. By including electrical conductors for transmitting control signals and/or power to the pumping system, the problem of power supply and operation is solved. The combination of electrical components to power and control the pumping system with an electro-fluidic system to allow flow from the reactors to the DHM and back, makes for a more efficient way to operate the digital holographic microscope system by reducing the number of wires and connections necessary to make all elements and the entire system operational. Not only does this simplify the physical configuration greatly, it also guarantees that the pumping system and the electro-fluidic system are configured correctly with respect to the DHM. For instance, by defining flow rates, sampling intervals, sampling time, pressure differences, etc., programs can be used execute the sampling process according to the wishes of the operator.

In a preferred embodiment, the electrical conductors are at least partially integrated with the tubes, for instance by attaching them thereto and enclosing conductors and tubes in a single sheathing. Preferably the conductors are near or attached to the tubes at the first connector of the electro-fluidic system. By introducing said first connector into a DHM, the electric and fluidic connections between electro-fluidic system and DHM are made in a single operation. Also, by reducing the number of connections needed to make the system operational, the danger of accidental switches that are liable to occur when dealing with high amounts of cables and tubes will be reduced, and also make the product easier to operate.

By combining electrical and fluidic conductors and tubes and using shared connector to a DHM, the electro-fluidic system can be set up in a minimal amount of actions in a plug-and-play approach, lowering the threshold for new operators and reducing configuration and operation effort for all operators.

In an embodiment, at least one electro-fluidic system comprises one or more tubes suitable for coming in direct contact with fluid from said reactor. Preferably said tubes comprise a bendable material which is still resistant against possible kinks. The advantage of using tubes in the electro-fluidic system for guiding the fluid is that they can be produced cheaply and can be made long enough for the application at hand, or can be combined to a long fluid-guiding channel. In a more preferred embodiment, only the tubes, more preferably easily replaceable tubes, may come in direct contact with the fluid of the reactor. Thereby, other components of the electro-fluidic system can be reused without the necessity of, possibly expensive, cleaning or decontamination procedures.

In a preferred embodiment, said tubes of the fluid microscope system comprise a part, preferably with a slab-like shape, which is at least partially transparent for the illumination means of said DHM and which has a shape suitable for said DHM, for obtaining phase information of said fluid sample. In this case, the tube can be lead to the DHM for direct analysis of its contents, i.e. there is no need for an extra component, which could lead to a more expensive system, or to leaks in the electro-fluidic system due to bad or wrong connections between a tube and the extra component. In a further preferred embodiment, said DHM is capable of working in transmission mode and said tube has a shape comprising two parallel sides, transparent for the illumination means of said DHM. In another further preferred embodiment, said DHM is capable of working in reflection mode and said tube comprises at least one, preferably flat, side which is transparent for the illumination means of said DHM.

For inline monitoring and/or analyzing of a reactor with a DHM, optical contact is needed between DHM and at least a sample of the reactor's content, preferably without the need to remove that sample from the reactor completely, hence 'inline'. Therefore, one or more tubes of the electro-fluidic systems may comprise at least a part which provides optical contact with the DHM, preferably the properties of said part are optimized to the specifications of the DHM. Furthermore, in a preferred embodiment, the electro-fluidic system comprises one or more tubes for guiding a sample of the contents of the reactor to the DHM and back to the reactor and/or to another reactor. In such an embodiment, the electro-fluidic system leads fluid from one reactor to the DHM and then either back to the same reactor, or to another, possibly depending on the images obtained by the DHM, or to the same reactor but at a different position/height, etc. Since the DHM is able to acquire information about the sample fast and accurately, it can use this information in real-time to decide what needs to be done with the content of the observed sample. Thereto, in the current embodiment, the electro-fluidic system may comprise one or more, preferably electronically steered, valves and a decision-making unit which is operably connected to the valves and the DHM and which decides on which valves to open and/or close at which time, depending on the information required by the DHM.

To avoid contamination of the sample taken from one reactor e.g. by remains from another reactor, the parts of the electro-fluidic system circuits which may come into direct contact with fluids from reactors, should be easily replaceable. In this way, the parts that do not come into contact with fluid from reactors, can be reused. This has many advantages: the replaceable parts may at least partly be made from cheap materials, only the part which should provide optimal optical contact with the DHM may need to be expensive, the re-usable parts may be more expensive and of better quality as they will need to last a longer time. If the re-usable parts are cheap to manufacture, this is also fine. More in particular, the manufacturer of the system of the present invention has a choice in how to make the re-usable parts which can be optimized according to the specific use of the system. Replaceable parts of the system do not need to be decontaminated or sterilized, hereby gaining time and saving costs, but can be produced in large quantities, leading to reduced costs. Therefore, in a preferred embodiment, the electro-fluidic system comprises tubes which are easily replaceable and/or cheap to manufacture.

It is often desirable that a continuous fluid flow can be induced in at least one of the electro-fluidic systems. This allows sampling of the contents of the reactor in time and monitoring of different samples to obtain a better knowledge of the state and/or reactions of the reactor. A continuous fluid flow may be present due to natural phenomenon such as convection, conduction or radiation, by density or pressure differences induced by e.g. the reactions taking place in the reactor or heat gradients, by gravity, etc. However, this cannot be guaranteed in all situations, or is simply too impractical naturally provide at desired rates. Furthermore, it is often desirable that a stepwise fluid flow can be induced in at least one of the electro-fluidic systems. To remedy this, the current embodiment of the invention comprises a pumping system, capable of inducing fluid flow in one or all of the tubes of the electro-fluidic system. The pumping system is arranged to be electronically steered and/or powered by the DHM by means of the electrical conductors of the electro-fluidic system which can be connected between the DHM and the pumping system, at least partially running along the tubes from the DHM to the pumping system.

In a preferred embodiment, the present invention provides a fluid microscope system as described above, whereby at least one pumping system comprises a continuous pump, capable of inducing a continuous fluid flow in an electro-fluidic system to which said continuous pump is connected. In a more preferred embodiment, said pump is a diaphragm pump. In an alternative embodiment, said pump is a peristaltic pump. A continuous flow may result in a higher throughput and therefore a faster analysis or better monitoring of the processes in the reactor and electro-fluidic system. Furthermore, due to its fast acquisition time, a DHM is capable of acquiring high-quality holographic images of a sample, even if a continuous flow is present in said sample. More preferably, the electro-fluidic system comprises at least one valve system for allowing fluid flow through the tubes of the electro-fluidic system in a single direction for each tube. Most preferably, the valve system is combined with the pumping system to provide a fluid flow through the tubes in a single direction.

In an alternatively preferred embodiment, said fluid microscope system comprises a pumping system which comprises a stepwise pump, capable of inducing a stepwise fluid flow in an electro-fluidic system to which said stepwise pump is connected. A stepwise fluid flow may be desired when the DHM is e.g. desired to perform scans which take a certain amount of time. In a stepwise flow, the fluid sample may remain stationary for at least a part of the pumping cycle. During this stationary phase, the DHM may scan or observe the sample over a large area. In a more preferred embodiment, said pump is a diaphragm pump. More preferably, the electro-fluidic system comprises at least one valve system for allowing fluid flow through the tubes of the electro-fluidic system in a single direction for each tube. Most preferably, the valve system is combined with the pumping system to provide a fluid flow through the tubes in a single direction.

In a preferred embodiment, said tube comprises a part which is at least partially transparent for the illumination means of said DHM and which comprises a flow cell and/or a microfluidic system. In a more preferred embodiment, said flow cell and/or microfluidic system comprises a cross section in which the height and/or width varies along the cross section. This allows obtaining clear holographic images for a variety of concentrations of objects suspended in the fluid. A high concentration of suspended objects could lead to a large number of objects being stacked on top of one another and may lead to difficulties in obtaining a holographic image, especially if the DHM works in transmission mode. A low concentration could result in the DHM obtaining holographic images of the fluid medium only and not of an object suspended in that medium. If the concentration is high, a holographic image can be obtained at the position where the height or width is small, thereby ensuring that not too many objects are stacked in the illumination beam. If the concentration is small, a holographic image can be obtained at the position where the height or width is large, thereby ensuring that at least one suspended object is in the illumination beam. In a more preferred embodiment, said microfluidic system comprises a branching of said tube in multiple tubes of preferably different cross sections, diameters, heights and/or widths. Such an arrangement also allows obtaining clear holographic images for a variety of concentrations of objects suspended in the fluid. Preferably, the cross section, diameter, height and/or width of said flow cell and/or microfluidic system is chosen in function of the size of the suspended objects and/or the size of the illumination beam of the DHM. More preferably, the narrowest dimension in a cross section of said flow cell and/or microfluidic system is larger than 10 micrometer, more preferably larger than 30 micrometer, even more preferably larger than 50 micrometer, and/or the largest dimension in a cross section of said flow cell and/or microfluidic system is smaller than 5000 micrometer, more preferably smaller than 3000 micrometer, even more preferably smaller than 2500 micrometer. In a preferred embodiment, said microfluidic system is attached on a substrate, as this is easy manufacturable and provides stability to the microfluidic system.

A system as disclosed in this text is suited to monitor multiple reactors or at least multiple samples, using a limited set of DHMs. In a preferred embodiment, the DHM of the present invention comprises a multiple-sample scanning system for observing or scanning multiple samples using the same DHM. This multiple-sample scanning system may comprise a scanning stage, which preferably is motorized, capable of moving multiple samples subsequently in the optical path of the illumination means of the DHM, and/or this multiple-sample scanning system may comprise an optical guiding system capable of changing the optical path of the illumination means of the DHM such that the multiple samples are subsequently placed in the illumination beam of the illumination means. Such an optical guiding system may comprise one or more mirrors, which may be or become partially transparent, optical fibers, liquid crystal devices, lenses, parabolic mirrors, etc. all of which may be motorized and, preferably, electromechanically and/or electronically steered. Therefore, in a preferred embodiment, the multiple-sample scanning system is operably connected to the DHM.

In a preferred embodiment, the system of the present invention comprises a central unit connected to the DHM or part of the DHM, which is capable of adjusting the DHM, in particular the working parameters of the DHM. In a more preferred embodiment, the system comprises a multiple-sample scanning system, operably connected to said central unit, whereby the central unit is capable of steering said multiple-sample scanning system, thereby subsequently selecting multiple samples for observation by said DHM.

In a preferred embodiment, the DHM comprises a multiple-sample scanning system for easily changing the position of the multiple samples or the path of the illumination beam of the illumination means of the DHM in order to stepwise observe multiple samples contained in different electro-fluidic systems/tubes. This system may comprise a set of optical components, such as mirrors, optical fibers, partially reflecting, opaque and/or transparent surfaces, prisms, lenses, beam splitters, etc., all of which may be electromechanically or electronically steered to reflect and/or transmit light into specific directions.

In a preferred embodiment, the fluid microscope system according to the present invention comprises at least one electro-fluidic system which comprises a reactor attachment system for easily attaching and/or detaching said electro-fluidic system to said reactor, whereby leakage of fluid is prevented. In a more preferred embodiment, said reactor attachment system comprises a screw thread mounted on an outer surface which can be screwed into and out of a corresponding screw thread in an opening of a side or lid of said reactor, hereby sealing said opening, i.e. preventing fluid from escaping the volume created by said reactor and said electro-fluidic system, whereby said reactor attachment system comprises at least two passageways for fluid in-flux and fluid out-flux, hereby allowing transport of fluid from said reactor to said DHM and back via said electro-fluidic system. The reactor attachment system can be such that the electro-fluidic system can be connected to a reactor from the top, the side, the bottom or a combination thereof.

In a second aspect, the present invention provides an electro-fluidic system for a fluid microscope system for analyzing and/or monitoring the contents of one or more fluid-based reactors or canalizations, comprising:

a. one or more tubes for guiding a fluid flow between the DHM and the reactors of said system, whereby said one or more tubes are suitable for coming in direct contact with fluid from said reactors and comprise:
  i. a first connector at the proximal end, suitable for being operatively received in the DHM and preferably a second connector at the distal end, suitable for being operatively connected to one of said reactors;
  ii. and a part which is at least partially transparent for the illumination means of said DHM for obtaining holographic information of said fluid sample;
b. mounting means arranged for mounting a pumping system onto said tubes to induce a fluid flow;
c. optionally a pump system, arranged to be mounted on the mounting means and arranged for inducing fluid flow in said tubes, characterized in that said electro-fluidic system comprises one, two or more electrical conductors for transmitting electrical signals and/or electrical power to a device mounted on said mounting means, and said electrical conductors are arranged and attached at least partially along one of said tubes, and whereby one end of said conductors is attached to the first connector, and the other end to the mounting means. The partially transparent part of the one or more tubes has a shape suitable for the DHM.

Preferably, said mounting means are located on the tubes towards the distal end of said tubes.

An electrically conducting hydraulic hose has been described in U.S. Pat. No. 3,749,814. The device therein formulated lacks several vital components of the electro-fluidic system according to the present invention, such as being of a material that allows contact with the fluid from the reactors, a partially transparent part for the illumination means of a DHM, mounting means for a pump. The electro-fluidic system as described in this document is therefore a great improvement on said hydraulic hose and does not infringe upon it.

A pumping system generally comprises a pump, such as a diaphragm pump, a power source, such as a battery or alternatively it can be powered by an electrical connection to a controller such as a DHM, and optionally comprises a valve system. The power source is preferably rechargeable and/or spatially removable from said pumping system. The power source will commonly be an expensive part and delicate for cleaning and sterilization purposes. By making said power source spatially removable, the electro-fluidic system can be cleaned more easily and sterilized in an autoclave as the other elements are more robust, or can easily and cheaply be made so.

As mentioned above, the electro-fluidic system comprises one or more tubes which comprise a part which is at least partially transparent for the illumination means of a DHM of said fluid microscope system for obtaining phase information of a fluid sample in said tubes, and a mounting means, arranged for mounting a pumping system. Said mounting means allows operative coupling of a pumping system to the electro-fluidic system, such that a pump system mounted on said mounting means can induce a fluid flow in the electro-fluidic system. Furthermore, said tubes may have any of the specifications already described above.

The mounting means allow operative coupling of a pumping system to the electro-fluidic system. The mounting means are attached to at least one, and preferably all tubes of the electro-fluidic system. Preferably the mounting means are attached around one or more of the tubes of the electro-fluidic system. The mounting means may comprise a connector, such as a snap-fit connector, a screw-type connector, a magnetic connector, etc., the connector configured to allow a pumping system to be mounted on the mounting means via said connector. Alternatively or additionally, the mounting means may comprise a housing arranged for receiving a pumping system. Further, the mounting means may comprise an electrical plug or socket which is internally connected to the other end of the electrical conductors, and which is configured to connect to a corresponding socket or plug of the pumping system to allow the DHM to control and/or to provide power to the pumping system. The mounting means may further comprise a membrane which is connected to or which is integrally part of at least one of the tubes of the electro-fluidic system and which can move such that the inner volume of the at least one tube is changed, thereby applying pressure on a fluid within the tube to make the fluid flow. The membrane hereby can be connected, e.g. mechanically or magnetically, to a pumping system, and preferably with an actuator head thereof, when the pumping system is mounted on the mounting means. Alternatively or additionally, the mounting means may comprises a pressure region at the location of a tube of the electro-fluidic system, preferably the pressure region in the shape of a slit or through-hole, at which pressure region a pumping system, and preferably an actuator head thereof, is allowed to directly exert a pressure on said tube for creating a pressure difference in a fluid within said tube to make the fluid flow.

In a preferred embodiment, the present invention provides tubes as described above, whereby said tubes are autoclavable, i.a. resistant to temperatures and pressures typically used in an autoclave to sterilize the tubes.

In a preferred embodiment, the present invention provides tubes as described above, whereby said part comprises a flow cell and/or a microfluidic system. Such tubes offer the benefits of a flow cell and/or microfluidic system as described previously in this document.

In a preferred embodiment said at least partially transparent part preferably has a shape suitable for said DHM, preferably a slab-like shape, more preferably a shape comprising two parallel sides, preferably when said DHM works in transmission mode, and/or whereby said at least partially transparent part preferably comprises at least one flat side preferably when said DHM works in reflection mode.

In a preferred embodiment, at least one tube of said electro-fluidic system comprises a fluid-tight flexible part which, when compressed, pulled and/or pushed, results in a fluid flow in said tube. Said part can be manipulated manually. In a preferred embodiment, a pumping system can be operatively coupled to said part and to the electrical conductors that run at least partially along said tube. Preferably said pumping system can be steered remotely by an operator and/or powered through said electrical conductors from the DHM. Said pumping system may also be controllable directly from the pumping system itself. Some of the ways in which a pumping system may operate have been described above. Most preferably, the pumping system comprises a diaphragm pump.

In a preferred embodiment, one or more of said tubes comprise a valve system. Said valve system allows flow through the tubes in only one direction, which can for instance allow flow through a tube from a reactor to a DHM for analysis, without allowing said flow, or sample, to flow back to the reactor as it may be contaminated in some way. Another tube may then direct the analyzed sample to a second reactor, vessel, refuse container, etc., depending on further use. Said other tube may or may or may not be fitted with a similar valve system to avoid backflow towards the DHM. Preferably the valve system is located near the mounting means for the pump system. Preferably a valve system as in U.S. Ser. No. 08/356,670; is used.

In a preferred embodiment, said tubes of an electro-fluidic system are capable of forming a closed circuit for fluid flow between a reactor, a DHM and back to said reactor.

The electro-fluidic system of the present invention has the advantage of being able to non-destructively monitor the contents of a reactor when used in a fluid microscope system as described above. Thereby, it is possible to re-introduce the samples which are observed in the DHM to the reactor. Therefore, in a preferred embodiment, at least one electro-fluidic system forms a closed circuit between one of said reactors and said DHM and back to said reactor, i.e. said electro-fluidic system is capable of guiding fluid from said reactor to said DHM and back. In some set-ups, it may be beneficial to lead observed samples to another reactor. Therefore, in a preferred embodiment, the system of the present inventions comprises at least one electro-fluidic system whereby said electro-fluidic system forms a circuit between said reactor and said DHM and another reactor, i.e. said electro-fluidic system is capable of guiding fluid from said reactor to said DHM and subsequently to said other reactor. Furthermore, in a preferred embodiment, the system of the present invention comprises at least one electro-fluidic system which forms a circuit between a first reactor and the DHM, and between the DHM to said first and at least one other reactor, whereby said electro-fluidic system preferably comprises a switching mechanism which is capable of selecting first and/or other reactors to be connected to the DHM such that the fluid sample observed by the DHM is guided to the selected reactor, preferably depending on an analysis of said sample. Such a system can be used to separate the contents of a reactor according to pre-defined characteristics.

As mentioned above, the electro-fluidic system comprises electrical conductors, running at least partially along said tubes, whereby said electrical conductors can transmit electric signals and/or power to a pumping system when it is mounted on the mounting means. In a preferred embodiment, said electrical conductors form a closed electrical circuit between a controller, preferably a DHM, and a pumping system when the electro-fluidic system is operatively coupled to the DHM and the pumping system is mounted on the mounting means.

In a preferred embodiment, said electrical conductors run along one or more tubes of the electro-fluidic system at the distal end of both tubes and electrical conductors. In this embodiment, the DHM is adapted to operatively receive the first connector of the tubes, thereby operatively coupling said tubes and said electrical conductors to said DHM.

In a further preferred embodiment, said electrical conductors run along one or more tubes of the electro-fluidic system near the mounting means. The electrical conductors are preferably connected to the mounting means for transmitting electrical signals and/or power to a pumping system when said pumping system is mounted on the mounting means.

In a further preferred embodiment, the mounting means of the electro-fluidic system is adapted to easily accommodate a pumping system. This is exacted by configuring the mounting means so that upon mounting the pumping system thereupon, said pumping system controls fluid flow in the tubes of said electro-fluidic system and is electrically connected to the electrical conductors of the electro-fluidic system. Due to said electrical connection, the pumping system can be controlled and/or powered by a controller electrically connected to the electrical conductors. This also facilitates the installation of the pumping system as it reduces the number of connections needed to execute manually. Furthermore, this brings a plug-and-play approach when mounting a pumping system on the mounting means.

In a further preferred embodiment, said electrical conductors are integrated into the part of the tube that is operatively received by the DHM, the first connector, so that the operative coupling of the tubes and the electrical conductors to the DHM is executed by introducing said first connector.

In a most preferred embodiment, the electrical conductors of an electro-fluidic system run along the tubes of said electro-fluidic system over the entire length of the electrical conductors, is integrated into the first connector of the electro-fluidic system, and can be electrically connected with a DHM through the introduction of said first connector into said DHM.

In a preferred embodiment, the electro-fluidic system comprises a pumping system arranged for inducing fluid flow in one or more tubes of said electro-fluidic system and arranged for receiving control signals and/or power from a controller, through an electrical connection by the electrical conductors from said controller to the pumping system. Some of the ways in which said pumping system may operate, have been described above, as has been the way in which said pumping system can be operatively coupled to both said tubes and said electrical conductors.

In a further preferred embodiment, said pumping system is removably attached to said electro-fluidic system, and can be operatively coupled to the electrical conductors of said electro-fluidic system and is capable of inducing a fluid flow in one or more tubes of said electro-fluidic system through automatic control through a controller.

In a further preferred embodiment, said pumping system comprises a power source. Said pumping system can be powered by said power source or through electrical conductors said pumping system can be operatively coupled to. In a further preferred embodiment, said power source is spatially removable and re-attachable. For practical purposes, a pumping system will often be included as a permanent part of an electro-fluidic system. The power source will commonly be an expensive part and delicate for cleaning and sterilization purposes. By making said power source re-attachable, the electro-fluidic system can then be easily cleaned and sterilized in an autoclave as the other elements are more robust, or can easily and cheaply be made so. This way, the power source can also be reused for other electro-fluidic systems or other purposes.

In a preferred embodiment, said electro-fluidic system comprises a sheathing for the protection of the tubes and the electrical conductors of said electro-fluidic system, whereby said sheathing encloses the tubes and the electrical conductors. This allows for an easy handling of the tube and the electrical conductors when it is transported. The tubes and the electrical conductors in a fluid microscope system such as described in this text are exchangeable and therefore should be easily to manipulate by the user. By using a sheathing that encloses the tubes and the electrical conductors, the number of wires and tubes visible and tangible for the operator is reduced, and thereby more efficient and practical in use.

In the most preferred embodiment, the present invention provides an electro-fluidic system which may contain any or all of the specifications described above, for a fluid microscope system which may contain any or all of the specifications described above.

The fluid microscope system may contain none, any or all of the specification described above. Often, the use of said system will dictate which specifications will be necessary.

In a third aspect, the present invention provides for a method for installing an electro-fluidic system, according to any as described above, in a fluid microscope system with one or more fluid-based reactors or canalizations, according to any as described above, comprising the following steps:
  a. operatively coupling said electro-fluidic system to one of said reactors or canalizations by connecting the second connectors of one or more tubes to said reactor or canalization;
  b. operatively coupling said electro-fluidic system to a DHM of said fluid microscope system by introducing the first connectors of said one or more tubes into said DHM;
  c. and operatively coupling a pumping system to said electro-fluidic system by mounting said pumping system on the mounting means of the electro-fluidic system.

The use of the electro-fluidic system and the fluid microscope system as described in this document, allows for an improved way of installing said electro-fluidic system. Due to the combination of the electrical conductors with the tubes of the electro-fluidic system and the configuration of the first connector of the electro-fluidic system, operatively connecting the electro-fluidic system to a DHM is achieved easily by introducing said first connector into said DHM. Due to the configuration of the mounting means of the electro-fluidic system, mounting the pumping system thereupon allows said the pumping system to control fluid flow through the tubes and allows the DHM to control and/or power said pumping system. The present invention hence minimalizes the risk of errors and the effort needed by an operator for installing an electro-fluidic system in a fluid microscope system by reducing the number of connections the operator has to make and by the plug-and-play configurations of the elements of the electro-fluidic device, which operatively connect elements upon introduction/reception.

In a fourth aspect, the present invention provides for a method for replacing an electro-fluidic system, according to any as described above, in a fluid microscope system with one or more fluid-based reactors or canalizations, according to any as described above, comprising the following steps:
  a. removing said electro-fluidic system from operative coupling with a DHM of said fluid microscope system;
  b. removing said electro-fluidic system from operative coupling with said one or more fluid-based reactors or canalizations;
  c. operatively coupling a replacement electro-fluidic system to one of said reactors or canalizations by connecting the second connectors of one or more tubes of the replacement electro-fluidic system to said one reactor or canalization;
  d. operatively coupling said replacement electro-fluidic system to a DHM of said fluid microscope system by introducing the first connectors of said one or more tubes of the replacement electro-fluidic system into said DHM;
  e. and operatively coupling a pumping system to said replacement electro-fluidic system by mounting said pumping system on the mounting means.

The removal of the old electro-fluidic system is made easy by the reduced number of connections needed for installation, as mentioned above, and therefore the reduced number of disconnections needed for removal. The method for installation of a replacement, e.g. a new or a cleaned, electro-fluidic system is improved for the reasons described above, facilitating the total process of replacement.

In a fifth aspect, the present invention provides for a method for observing and/or monitoring suspended objects in a fluid in a fluid-based reactor or canalization, comprising the following steps:
  a. inducing a fluid flow by a pumping system from said reactor or canalization to a DHM;
  b. capturing a sample and observing and/or monitoring said sample with the DHM;
  c. optionally inducing a fluid flow from said DHM to said reactor or canalization and optionally returning the sample to the fluid flow,
characterized in that the pumping system is controlled and optionally powered by said DHM.

In a preferred embodiment, the present invention provides for a method for observing and/or monitoring suspended objects in a fluid flow by a fluid microscope system with one or more fluid-based reactors or canalizations, according to any as described above.

In a preferred embodiment, said method comprises the following steps:
  a) inducing and controlling a fluid flow by a pumping system from said reactor or canalization to a DHM;
  b) capturing a sample at which point the fluid flow is stopped;
  c) observing and/or monitoring said sample with the DHM;
  d) releasing said sample and inducing and controlling a fluid flow by a pumping system, whereby said sample is optionally returned to said fluid-based reactor or canalization.

Note that the process of this method can be repeated at the end of each previous execution. This process can be automated by use of a sampling program by which the DHM electronically steers the pumping system according to the wishes of an operator, such as sampling interval, flow rate, sampling time, run time, etc.

In another embodiment, said method comprises the following steps:
  a) inducing and controlling a continuous fluid flow by said pumping system from said reactor or canalization to a DHM;
  b) observing and/or monitoring the continuous fluid flow with the DHM;
  c) and optionally returning the observed and/or monitored parts of the flow to the reactor or canalization.

Note that the last step can also involve releasing the observed and/or monitored parts of the flow and/or the entire flow to another reactor or container. This process can be automated by use of a sampling program by which the DHM electronically steers the pumping system according to the wishes of an operator, such as flow rate, run time, etc.

The invention is further described by the following non-limiting examples which further illustrate the invention, and are not intended to, nor should they be interpreted to, limit the scope of the invention.

The invention is further described by the following non-limiting examples which further illustrate the invention, and are not intended to, nor should it be interpreted to, limit the scope of the invention.

Example 1

Figure 3:
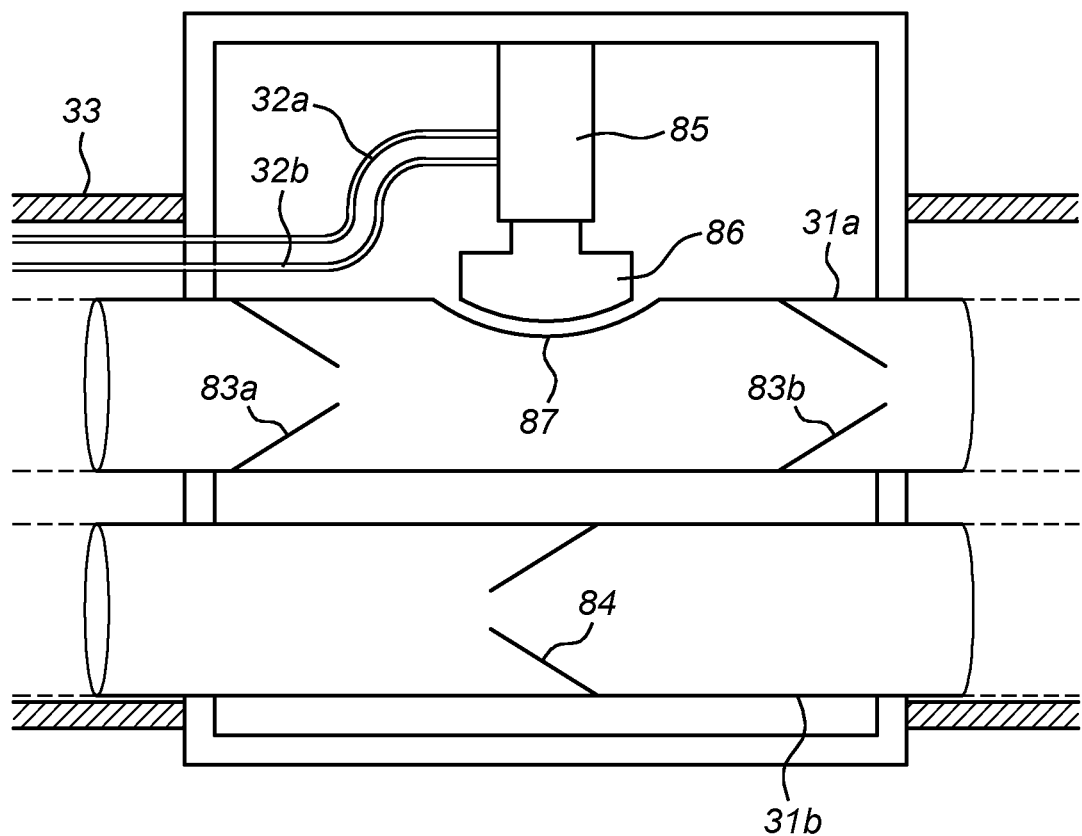
FIG. 3 shows a side view of two tubes on a mounting means. The first tube (31a) comprises two check valve systems (83 or 83a, 83b) in the part of the first tube that runs through the mounting means (81), the second tube (31b) comprises one check valve (84) system in the part of the second tube that runs through the mounting means (81), whereby the valve systems (83a, 83b) of the first tube are adapted to only allow flow from the distal end to the proximal end of the first tube (31a) and the valve system (84) of the second tube (31b) are adapted to only allow flow from the proximal end to the distal end of the second tube.
Figure 4:
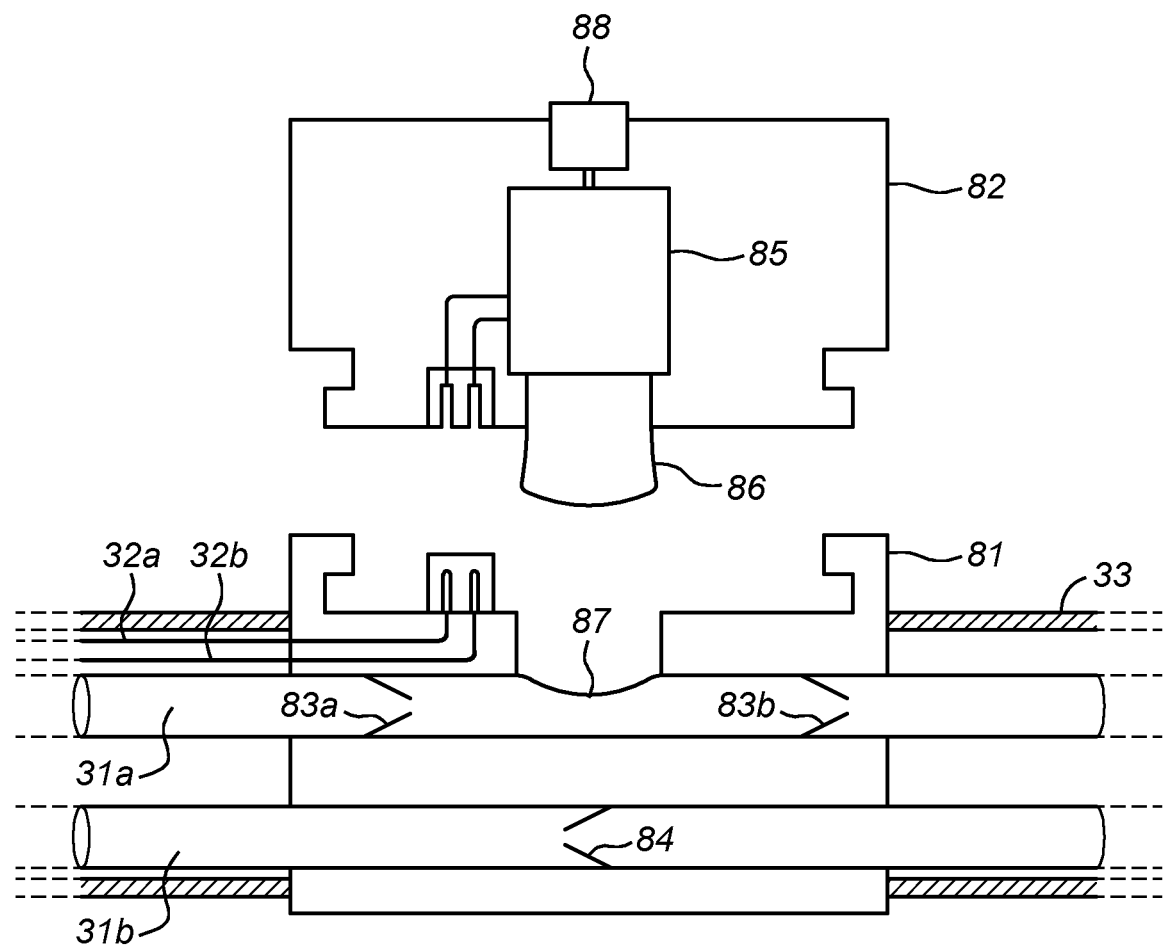
FIG. 4 shows the tubes in side view as in FIG. 3 with a control button (88) in the pumping system (82, 8).
Figure 5:
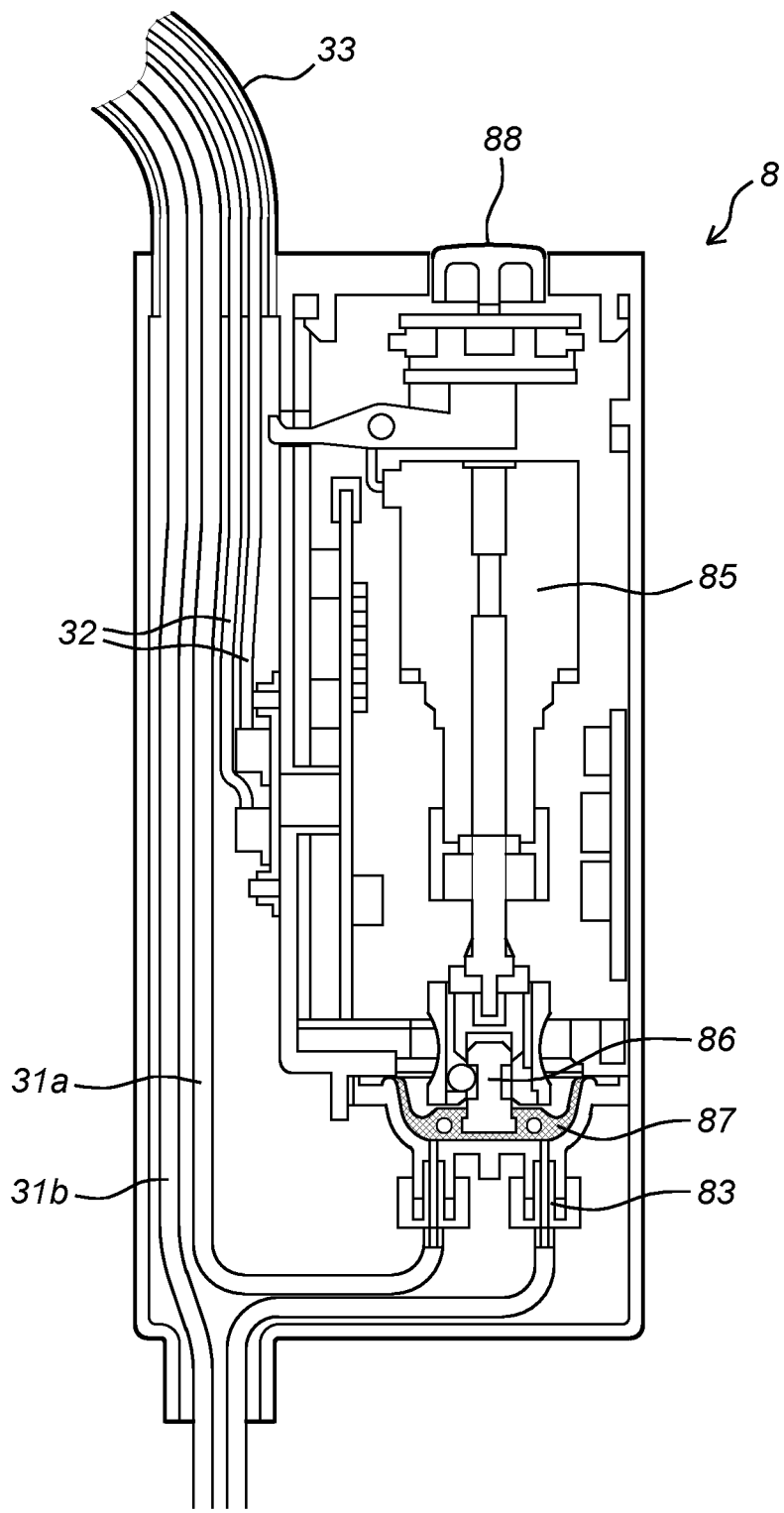
FIG. 5 shows the tubing system in cross-sectional view.

In the current embodiment as in FIG. 1, an electro-fluidic system 3 suitable for connection to a DHM (2) and to a fluid-based reactor 4 and for guiding fluid from said reactor to the DHM (2) and back, comprises two tubes, two electrical conductors, a sheathing, and a diaphragm pumping system on a mounting means for said diaphragm pumping system 8. The first tube is used for guiding fluid from the reactor to the DHM (2), the second tube is used for guiding fluid from the DHM (2) to the reactor. The tubes are suitable for coming in direct contact with fluid from the reactor and run along each other's full length. Said tubes are fluidly connected at the proximal end by a part (6) which is partially transparent for the illumination means (7) of the DHM (2). Said tubes share a first connector at the proximal end of the tubes suitable for being operatively received in the DHM (2), whereby upon introduction of said first connector into the DHM (2), the partially transparent part (6) is placed in the illumination means (7) of the DHM (2) whereby its contents can be observed. The tubes also share a second connector at the distal end of the tubes, whereby upon connection of said second connector to the reactor with a fluid-tight reactor attachment system (5), the tubes are fluidly connected to the reactor. As can be seen in FIG. 3, FIG. 4 and FIG. 5, The first tube (31a) comprises two check valve systems (83 or 83a, 83b) in the part of the first tube that runs through the mounting means (81), the second tube (31b) comprises one check valve (84) system in the part of the second tube that runs through the mounting means (81), whereby the valve systems (83a, 83b) of the first tube are adapted to only allow flow from the distal end to the proximal end of the first tube (31a) and the valve system (84) of the second tube (31b) are adapted to only allow flow from the proximal end to the distal end of the second tube. The check valve systems (83a, 83b) of the first tube (31a) are placed so as to have a part of the tube in between them that serves as a chamber for a diaphragm pump, having a membrane (87) as part of the walls of the chamber upon which the diaphragm pump (82) can exert force through an actuator (85) working an actuator head (86). Furthermore, the second connector comprises a reactor attachment system (5) for easily attaching and detaching the second connector to the reactor, whereby leakage of fluid is prevented. The electro-fluidic system also comprises two or more electrical conductors (32a, 32b), running along the tubes for the full length of said electrical conductors. The electrical conductors (32a, 32b) are connected to the first connector at the proximal end of said conductors (32a, 32b), so that, when the first connector is introduced in the DHM (2), said conductors (32a, 32b) are electrically connected to the DHM (2). The electrical conductors (32a, 32b) are connected to the mounting means (81), so that, when the diaphragm pumping system (82) is mounted on said mounting means (81), the conductors are electrically connected to said diaphragm pumping system (82). When the electro-fluidic system is operatively connected to a DHM (2) and a pumping system is mounted on the mounting means, the conductors (32a, 32b) form a closed electrical circuit between said DHM (2) and said diaphragm pumping system (82). The DHM (2), or a controller controlled by the DHM (2), transmits control signals and powers the diaphragm pumping system through the electrical conductors (32a, 32b). The sheathing (33) tightly envelops the conductors and the tubes from the first connector to the second connector for practical handling purposes whereby both tubes (31a, 31b), conductors (32a, 32b) and sheathing (33) are made of bendable material. The mounting system (81) is placed near the second connector and the chamber for a diaphragm pump, so that, when mounting the diaphragm pumping system (82) on said mounting means (81), the diaphragm pumping system (82) can induce fluid flow in the first tube. By the employment and positioning of check valves (83a, 83b), the diaphragm pumping system (82) can control these valves (83a, 83b) by inducing flow. As can be seen in FIG. 4 and FIG. 5, a control button (88) can be comprised in the pumping system (82, 8) that can initiate coupling and decoupling between the pumping system (82) and the mounting means (81) and/or start and shut down the pumping system (82).

By placing the mounting means (81), and thus the diaphragm pumping system (82) when mounted, close to the reactor, it will facilitate the process of inducing fluid flow. This is generally so for most pumping systems as they rely on creating pressure differences to cause fluid displacement. The further they are placed, the more fluid they will have to draw, which is less practical.

Figure 2:
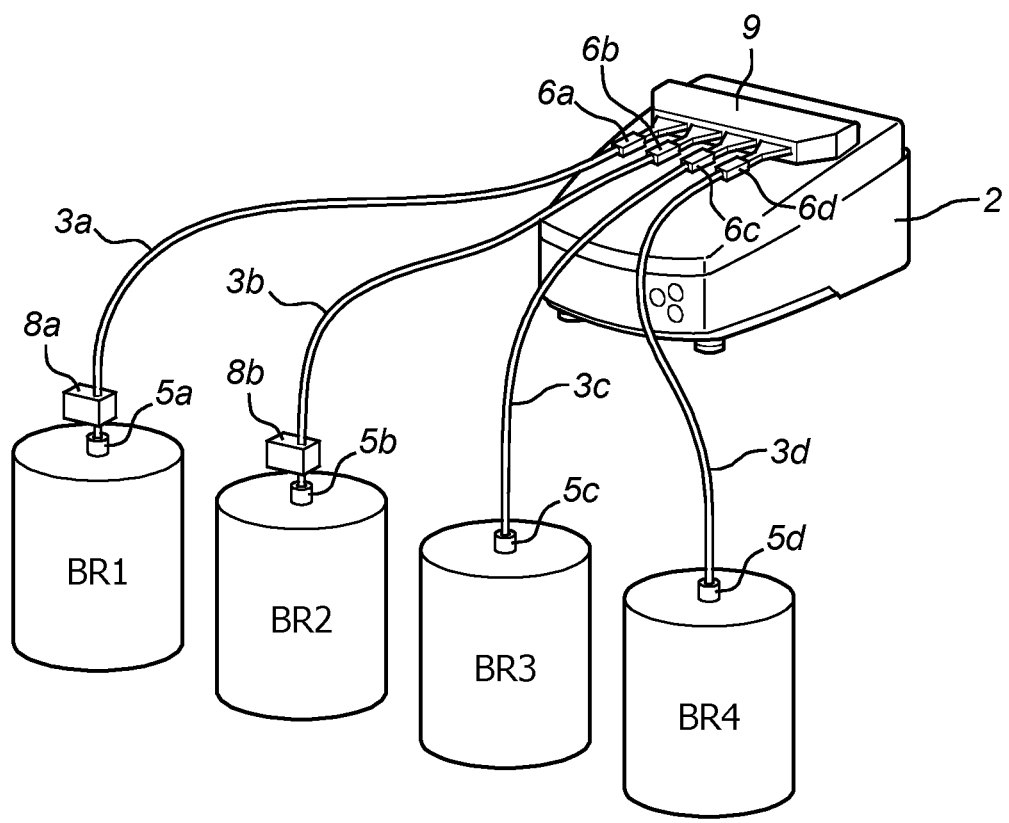
FIG. 2 shows an alternate embodiment in which a DHM (2) can be connected through multiple electro-fluidic systems (3a, 3b, 3c, 3d) to multiple fluid-based reactors (BR1, BR2, BR3, BR4).

In an alternate embodiment, a DHM (2) can be connected through multiple electro-fluidic systems (3a, 3b, 3c, 3d) to multiple fluid-based reactors (BR1, BR2, BR3, BR4), as shown in FIG. 2. In another alternate embodiment, a single electro-fluidic system can also connect multiple fluid-based reactors to a DHM.

Example 2

In an alternate embodiment, an electro-fluidic system is as described in example 1, except for the two tubes no longer running along each other's length and each having their own second connector, thereby allowing the electro-fluidic system to guide a flow from a first reactor to the DHM and then from the DHM to a second reactor when operatively coupled to said reactors and said DHM. The mounting means is located on the first tube, near the chamber for the diaphragm pumping system.

Example 3

In an embodiment, a fluid microscope system comprises a DHM capable of obtaining phase information of a fluid sample and comprising illumination means, and a single electro-fluidic system as described in example 1. Said DHM is provided with a controller unit that allows an operator to transmit control signals and power through the electrical conductors of the electro-fluidic system when operatively coupled. Operative coupling is achieved by introducing the first connector of the electro-fluidic system into the DHM, which has several ports adapted for receiving said first connector so that the possible samples in the partially transparent part of the electro-fluidic system can be observed with the DHM. As said, when the electro-fluidic system is coupled to the DHM, an electrical connection is made between the control unit of the DHM and the electrical conductors of the electro-fluidic system, and thereby to the diaphragm pumping system when it is mounted on the mounting means. The control unit can allow an operator to electronically steer the diaphragm pumping system directly, or can be set to run certain programmed settings, for instance setting a flow rate, a runtime, a sampling interval, etc.

Example 4

In an embodiment, a method for installing an electro-fluidic system as described in example 1 in a fluid microscope system with a reactor as described in example 3 comprises following steps:
 a. introducing the first connector of the electro-fluidic system into a port of the DHM, thereby electrically connecting the electrical conductors to the control unit of the DHM, and placing the partially transparent part of the electro-fluidic system in the DHM so it can be observed with the DHM;
 b. connecting the second connector of the electro-fluidic system to the reactor, thereby fluidly connecting the reactor to the tubes;
 c. and mounting a diaphragm pumping system on the mounting means of the electro-fluidic system, thereby electronically connecting said pumping system to the electrical conductors and thus to the control unit of the DHM and allowing the pumping system to induce fluid flow in the tubes.

What is claimed is:

1. A method for observing and/or monitoring suspended objects in a fluid in a fluid-based reactor or canalization, comprising the following steps:
 a. inducing a fluid flow from said reactor or canalization by an electrically powered pumping system;
 b. capturing a sample in the fluid flow and observing said sample with a Digital Holographic Microscope (DHM), wherein the pumping system is controlled and optionally powered by the DHM.

2. The method according to claim 1 further comprising the step:
 c. inducing a fluid flow from said DHM to said reactor or canalization.

3. The method according to claim 2 wherein step c. further comprises returning the sample to the fluid flow.

4. The method according to claim 3 wherein in step a., the fluid flow is induced and controlled by a pumping system, and wherein the fluid flow is induced from said reactor or canalization to the DHM.

5. The method according to claim 4 wherein in step b., the fluid flow is stopped when the sample is captured.

6. The method according to claim 5 wherein the DHM electronically steers the pumping system.

7. The method according to claim 6 wherein the fluid flow is a continuous fluid flow.

8. The method according to claim 5 wherein the pumping system comprises a diaphragm pump.

9. The method according to claim 1 wherein the sample is observed with the DHM in a flow cell and/or a microfluidic system.

10. The method according to claim 9 wherein said flow cell and/or microfluidic system comprises a cross section and has a height and/or width that varies along the cross section.

11. The method according to claim 1 wherein the DHM is a stand-alone DHM, and the electrically powered pumping system is fluidly connected to the DHM by external tubing.

* * * * *